US009969789B2

(12) United States Patent
Uger et al.

(10) Patent No.: US 9,969,789 B2
(45) Date of Patent: May 15, 2018

(54) TREATMENT OF CD47+ DISEASE CELLS WITH SIRP ALPHA-FC FUSIONS

(71) Applicant: TRILLIUM THERAPEUTICS INC., Toronto (CA)

(72) Inventors: Robert Adam Uger, Richmond Hill (CA); Penka Slavtcheva Slavova-Petrova, Toronto (CA); Xinli Pang, Brampton (CA)

(73) Assignee: TRILLIUM THERAPEUTICS INC., Toronto (CA)

( * ) Notice: Subject to any disclaimer, the term of this patent is extended or adjusted under 35 U.S.C. 154(b) by 0 days. days.

(21) Appl. No.: 14/653,165

(22) PCT Filed: Dec. 17, 2013

(86) PCT No.: PCT/CA2013/001046
§ 371 (c)(1),
(2) Date: Jun. 17, 2015

(87) PCT Pub. No.: WO2014/094122
PCT Pub. Date: Jun. 26, 2014

(65) Prior Publication Data
US 2015/0329616 A1 Nov. 19, 2015

Related U.S. Application Data

(60) Provisional application No. 61/738,008, filed on Dec. 17, 2012.

(51) Int. Cl.
*A61K 38/00* (2006.01)
*C07K 1/00* (2006.01)
*C07K 14/00* (2006.01)
*C07K 14/435* (2006.01)
*C07K 14/705* (2006.01)

(52) U.S. Cl.
CPC ........ *C07K 14/70503* (2013.01); *A61K 38/00* (2013.01); *C07K 2319/30* (2013.01)

(58) Field of Classification Search
None
See application file for complete search history.

(56) References Cited

U.S. PATENT DOCUMENTS

| 5,116,964 | A  | 5/1992  | Capon et al.    |           |
|-----------|----|---------|-----------------|-----------|
| 5,580,756 | A  | 12/1996 | Linsley et al.  |           |
| 5,844,095 | A  | 12/1998 | Linsley et al.  |           |
| 5,869,046 | A  | 2/1999  | Presta et al.   |           |
| 6,121,022 | A  | 9/2000  | Presta et al.   |           |
| 6,541,516 | B1 | 4/2003  | Narayanan et al.| 514/531   |
| 6,541,615 | B1 | 4/2003  | Ullrich et al.  | 536/23.1  |
| 6,913,894 | B2 | 7/2005  | Buhring et al.  | 435/7.21  |
| 7,282,556 | B2 | 10/2007 | Parkos          | 530/327   |
| 7,514,229 | B2 | 4/2009  | Jamieson et al. | 435/7.21  |
| 8,361,736 | B2 | 1/2013  | Majeti et al.   | 435/7.23  |
| 2002/0169303 | A1* | 11/2002 | Ullrich      | C07K 14/4703 536/23.1 |
| 2003/0026803 | A1 | 2/2003 | Barclay       | 424/144.1 |
| 2006/0135749 | A1 | 6/2006 | Matozaki et al. | 530/350 |
| 2008/0051556 | A1 | 2/2008 | Ullrich et al. | 530/300 |
| 2008/0107654 | A1 | 5/2008 | Kikuchi et al. | 424/139.1 |
| 2008/0131431 | A1 | 6/2008 | Smith et al.   | 424/134.1 |
| 2010/0239578 | A1 | 9/2010 | Danska et al.  | 424/134.1 |
| 2010/0239579 | A1 | 9/2010 | Smith et al.   |         |
| 2011/0014119 | A1 | 1/2011 | Jaiswal et al. | 424/1.49 |
| 2011/0237498 | A1 | 9/2011 | Raymond et al. | 514/1.7  |
| 2012/0189625 | A1 | 7/2012 | Wang et al.    | 424/134.1 |
| 2013/0011401 | A1 | 1/2013 | Huber et al.   | 424/136.1 |

FOREIGN PATENT DOCUMENTS

| EP | 2282772       | 1/2014   |
| JP | 2006-512894   | 4/2006   |
| JP | 2008-222711   | 9/2008   |
| WO | WO 94/29351   | 12/1994  |
| WO | WO 99/40940   | 8/1999   |
| WO | WO 00/66159   | 11/2000  |
| WO | WO 2004/029207 | * 4/2004 |
| WO | WO 2004/096133 | 11/2004  |
| WO | WO 2007045996 | 4/2007   |
| WO | WO 2007/092932 | 8/2007   |

(Continued)

OTHER PUBLICATIONS

Hatherly et al., "The Structure of the Macrophage Signal Regulatory Protein α (SIRPα) Inhibitory Receptor Reveals a Binding Face Reminiscent of That Used by T Cell Receptors," *J. Biol. Chem.* 282:14567, 2007.

International Search Report and Written Opinion for PCT/CA2013/001046, dated Mar. 5, 2012.

Armour et al., "Recombinant human IgG molecules lacking FCγ receptor I binding and monocyte triggering activities", *Eur. J. Immunol.*, 29:2613-2624, 1999.

Armour et al., "The contrasting IgG-binding interactions of human and herpes simplex virus Fc receptors", *Biochemical Society Transactions*, 30(4):495-500, 2002.

Extended European Search Report from related European Application No. 10774475.7, dated Sep. 9, 2012, 7 pages.

(Continued)

*Primary Examiner* — Alana Harris Dent
(74) *Attorney, Agent, or Firm* — Norton Rose Fulbright US LLP

(57) ABSTRACT

CD47+ disease cells, such as CD47+ cancer cells, are treated with an agent that blocks signalling via the SIRPα/CD47 axis. The agent is a human SIRPα fusion protein that displays negligible CD47 agonism and negligible red blood cell binding. The fusion protein comprises an IgV domain from variant 2 of human SIRPα, and an Fc having effector function. The IgV domain binds human CD47 with an affinity that is at least five fold greater than the affinity of the entire extracellular region of human SIRPα. The fusion protein is at least 5 fold more potent than a counterpart lacking effector function.

4 Claims, 7 Drawing Sheets

(56) References Cited

FOREIGN PATENT DOCUMENTS

Figure 1:
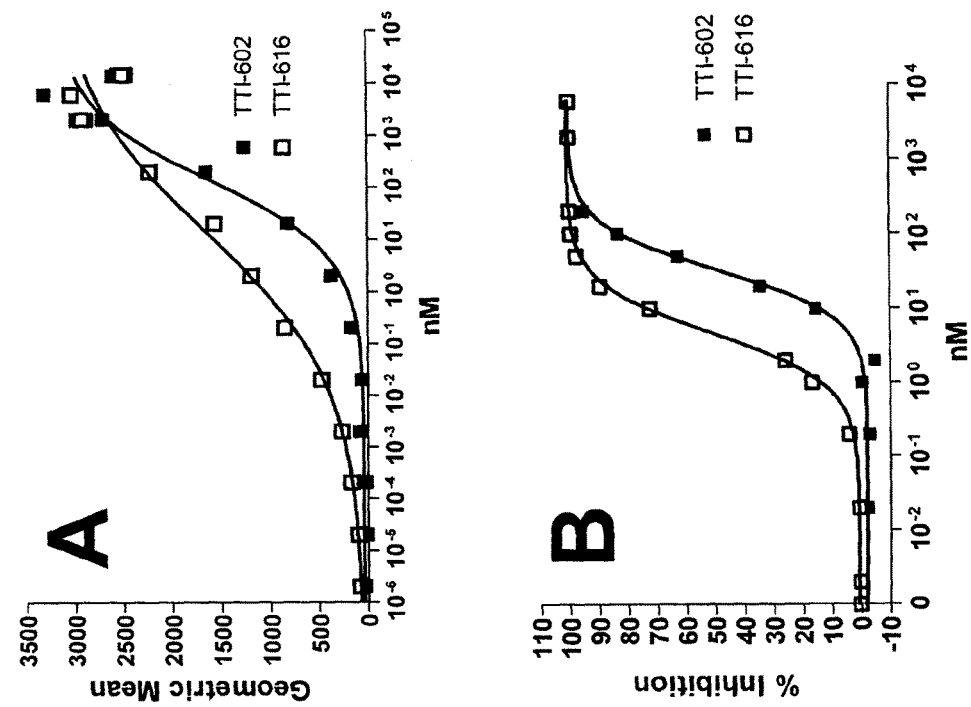

| WO | WO 2009046541 | | 4/2009 |
|---|---|---|---|
| WO | WO 2009/065541 | | 5/2009 |
| WO | WO 2009/091601 | | 7/2009 |
| WO | WO 2009/131453 | | 10/2009 |
| WO | WO 2010/070047 | | 6/2010 |
| WO | WO 2010/130053 | | 11/2010 |
| WO | WO 2011143624 | | 11/2011 |
| WO | WO 2013/109752 | * | 1/2012 |
| WO | WO 2012/083370 | | 6/2012 |
| WO | WO 2013/109752 | | 7/2013 |
| WO | WO 2013109752 | | 7/2013 |
| WO | WO 2013119714 | | 8/2013 |

OTHER PUBLICATIONS

Florian, et al., "Evaluation of normal and neoplastic human mast cells for expression of CD172a (SIRPa), CD47, and SHP-1", Journal of Leukocyte Biology, vol. 77, No. 6, 2005, pp. 984-992.
Ide, et al., Role for CD47-SIRPa signaling in xenograft rejection by macrophages, Proceedings of the National Academy of Sciences, National Academy of Sciences, US, vol. 104, No. 12, 2007, pp. 5062-5066.
International Search Report issued in PCT Application No. PCT/CA2010/000743, dated Aug. 9, 2010.
Jaiswal, S. et al., "CD47 is upregulated on circulating hematopoietic stem cells and leukemia cells to avoid phagocytosis", Cell 138(2):271-85, 2009.
Lamy, et al., "CD47 and the 19 kDa Interacting Protein-3 (BNIP3) in T Cell Apoptosis*", The Journal of Biological Chemistry, vol. 278, No. 26, Issue of Jun. 27, 2003, pp. 23915-23921.
Liu et al. (J. Mod. Biol. 365(3): 680-693, Jan. 19, 2007).
Majeti, "CD47 Is an Independent Prognostic Factor and Therapeutic Antibody Target on Human Acute Myeloid Leukemia Stem Cells", Blood, (ASH Annual Meeting Abstracts), No. 112: Abstract 766, 2008, 1 page.
Majeti, R. et al., "CD47 is an adverse prognostic factor and therapeutic antibody target on human acute myeloid leukemia stem cells", Cell 138(2):286-99, 2009.
Matozaki, T. et al., "Functions and molecular mechanisms of the CD47-SIRPalpha signaling pathway", Trends Cell Biol. 19:72-80, 2009.
Office Action from related Japanese Application No. 2012-510083, dated Jun. 24, 2014, 12 pages.
Office Communication issued in Chinese Patent Application No. 201080021398.7, dated Jun. 6, 2013.
Patent Examination Report from related Australian Patent Application No. 2010246872, dated Dec. 20, 2013, 5 pages.
Petrova, et al., "Lack of CD47 membrane mobility contributes to the poor erythrocyte binding of SIRPaFc, a novel CD47-blocking cancer immunotherapeutic", American Association for Cancer Research, Annual Meeting, Philadelphia, 2015, presentation abstract, 2 pages.
Pettersen, et al., "CD47 Signals T Cell Death", J. Immunol, No. 162, 1999, pp. 7031-7040.
Ritchie, D. S. et al., "A new therapeutic target for leukemia comes to the surface", Cell 138(2):226-28, 2009.
Sano, S. et al., "Gene structure of mouse BIT/SHPS-1", Biochem. J. 344 (3):667-75, 1999.
Shultz, L. D. et al., "Multiple defects in innate and adaptive immunologic function in NOD/LtSz-scid mice", J. Immunol. 154:180-91, 1995.
Takenaka, K. et al., "Polymorphism in Sirpa modulates engraftment of human hematopoietic stem cells", Nat. Immunol. 8:1313-23, 2007.
Uger, et al., "Cancer immunotherapy targeting CD47: Wild type SIRPaFc is the ideal CD47-blocking agent to minimize unwanted erythrocyte binding", American Association for Cancer Research, Annual Meeting, San Diego, 2014, presentation abstract, 1 page.
Van, et al., "CD4Low Status on CD4 Effectors Is Necessary for the Contraction/Resolution of the Immune Response in Humans and Mice", PLoS One, vol. 7, Issue 8, e41972, Aug. 2012, pp. 1-10.
Wang, J. C. et al., "Cancer stem cells: lessons from leukemia", Trends Cell Biol. 15:494-501, 2005.
Wines et al., "The IgC Fc Contains Distinct Fc Receptor (FcR) Binding Sites: The Leukocyte Receptors FcyRI and FcyRIIa Bind to a Region in the Fc Distinct from That Recognized by Neonatal FcR and Protein A", The Journal of Immunology, 164:5313-5318, 2000.
"Untitled document describing methodology, showing charts" cited as Non-Patent Literature filed during the Opposition Procedure for European Application No. 1077475.7, dated Aug. 2, 2016.
Barclay et al, "The SIRP family of receptors and immune regulation", Nature Reviews, dated Jun. 2006, vol. 6, pp. 457-464.
Econotnides et al., (2003) Nature Medicine 9(1): 47-52.
European Search Report and Search Opinion in related European Application No. 15160169.7, dated Dec. 1, 2015, 7 pages.
Experimental Report, cited as D1O in opposition filed by John Gerard Leeming in related European Application No. 10774475.7 dated Feb. 8, 2016, 6 pages.
Holash et al., (2002) PNAS 99(17): 11393-11398.
Information about the result of Oral Proceedings for European Application No. 10774475.5, dated Nov. 6, 2017.
International Search Report issued in PCT Application No. PCT/NL2009/050220 (WO2009/131453).
Jaiswal et al: "Macrophages as mediators of tumor immunosurveillance", Trends Immunol, Jun. 2010, 31(6):212-219.
Letter regarding the opposition procedure (no time limit) (Submissions re EU 2429574 B1, opposed by James Poole Limited), filed Feb. 8, 2016.
Letter regarding the opposition procedure (no time limit) Comments from JA KEMP re EU 10774475.7 and opposition by John Gerard Leeming), filed Sep. 6, 2017.
Liu et al., "Functional Elements on SIRPα IgV domain Mediate Cell Surface Binding to CD47," J. Mol. Biol., 2007; 365(3): 680-693.
Majeti et al: "CD47 is an adverse prognostic factor and therapeutic antibody target on human acute myeloid leukemia stem cells", Developmental Cell, Cell Press, Cambridge, MA, US, vol. 138, No. 2, Jul. 23, 2009, pp. 286-299.
Majeti, "CD47 is an Independent Prognostic Factor and Therapeutic Antibody Target on Human Acute Myeloid Leukemia Stem Cells", Blood, (ASH Annual Meeting Abstracts), No. 112: Abstract 766, 2008, 3 pages.
Nierkens et al. The Journal of Immunology 2005, 175:3707-3714.
Office Action issued in Chinese Application No. 201380073010.1, dated Jun. 1, 2017 (English Translation Provided).
Office Action issued in related Japanese Application No. JP 2015-160462, dated Jun. 8, 2016 (English Translation included).
Opposition filed by James Poole Limited in related European Application No. 10774475.7 dated Feb. 8, 2016.
Opposition filed by John Gerard Leeming in related European Application No. 10774475.7 dated Feb. 8, 2016.
Perrin et al. 1996, J. Neuroimmunol. 65:31-39.
Preliminary Observations - Sununons dated Oct. 4, 2017 in Opposition Proceedings for Application No. 10774475.7.
Reid, Ronald E., Ed., "Peptide and Protein Drug Analysis", Marcel Dekker, Inc., New York: 2000, p. 616.
Reply of the patent proprietor to the notice(s) of opposition re EU 2429574, dated Sep. 5, 2017.
Response to Communication Pursuant to Rules 70(2) and 70a(2) EPC filed in European Application No. 10774475.7 dated Mar. 29, 2013.
Response to the Communication Pursuant to Article 94(3) EPC filed in European Application No. 10774475.7 dated Jun. 12, 2014 •.
Sandbom et al., Gastroenterology 2001;121:1088-1094.
Seiffert et al., "Signal-regulatory protein a (SIRPα) but not SIRPβ is involved in T-cell activation, binds to CD47 with high affinity, and is expressed on immature CD34+CD38-hematopoietic cells", Blood, May 1, 2001, vol. 97, No. 9, pp. 2741-2749.
Soto-Pantoja et al. (2012), PNAS 109(42):E2842-5.
Supplementary European Search Report and Opinion for EP 10774475, search completed Aug. 27, 2012.
Theocharides et al. 2012, J. Exp. Med. 209(10)1883-1899.

(56) References Cited

OTHER PUBLICATIONS

Umemori, Hisashi et al., Journal of Biological Chemistry 283(49):34053-34061 (Dec. 5, 2008).
Vernon-Wilson et al., (2000) Eur. J. Immunol. 30: 2130-2137.
Willingham et al. (2012), PNAS 109(42):E2844-E2845.
Willingham et al., "The CD47-signal regulatory protein alpha (SIRPα) interaction is a therapeutic target for human solid tumor," PNAS 2012; 109(17):6662-6667.
Zhao et al. Blood 2012; 119:4333-4.
Zhao et al., (Apr. 2009) European Journal of Clinical Investigation, 39(Suppl. 1), Abstract 636.
Examination Report No. 2 for Australian Patent Application AU2013362789, dated Sep. 15, 2017.

* cited by examiner

CD47+ human Jurkat T cells were incubated with SIRPαFc fusion proteins or control Fc (3 μM) or left untreated (UT) overnight and then stained for Annexin-V and 7-AAD and analyzed by flow cytometry. The pro-apoptotic agent staurosporine (Staur) at 1 μM was included as a positive control. One sample containing TTI-602 was pretreated with B6H12, a CD47-blocking antibody [Data from Exp #280].

TREATMENT OF CD47+ DISEASE CELLS WITH SIRP ALPHA-FC FUSIONS

CROSS-REFERENCE TO RELATED APPLICATIONS

This application is a national phase application under 35 U.S.C. § 371 of International Application No. PCT/CA2013/001046 filed 17 Dec. 2013, which claims priority to U.S. Provisional Application No. 61/738,008 filed 17 Dec. 2012. The entire contents of each of the above-referenced disclosures is specifically incorporated by reference herein without disclaimer.

FIELD OF THE INVENTION

This invention relates to therapeutic, Fc fusion proteins useful particularly for the treatment of subjects presenting with CD47+ disease cells. The fusion proteins are based on a domain within the extracellular region of human SIRPα, and incorporate an Fc region that enhances the anti-cancer effect of the fusion protein.

BACKGROUND OF THE INVENTION

Signal regulatory protein alpha (SIRPα) is a transmembrane protein belonging to the immunoglobulin superfamily, and a receptor for CD47. Cloning and expression of a human form of SIRPα has been described by Ullrich et al in U.S. Pat. No. 6,541,615. Involvement of SIRPα and CD47 in the etiology of cancer and other diseases has been implicated by Sarfati et al in WO1999/040940 and by Van den Berg et al in WO00/66159, who suggest therapeutic use of an inhibitor of SIRPα. More recently, Jaiswal et al have suggested the use of antibodies to CD47 for the treatment of hematopoietic cancers, in WO2009/091601. The interaction between SIRPα and CD47 plays an important role in regulating the phagocytosis of leukemia cells and leukemia stem cells (LSCs) by macrophages. Blocking antibodies against CD47 have been shown to promote phagocytosis of LSCs by macrophages. In addition, Wang et al have suggested cancer treatments based on SIRPα fusion proteins in WO 2010/130053. For treating immune disorders, Smith et al have suggested the use of CD47-based Fc fusions, in US2008/0131431. The treatment of inflammatory and immune disorders also is taught by Raymond et al, in WO2010/070047.

It would be useful to provide agents that inhibit signalling via the SIRPα/CD47 axis for use in the treatment of cancer and other diseases.

SUMMARY OF THE INVENTION

The present invention provides SIRPα as an Fc fusion protein in which components are selected for optimal inhibition of the CD47/SIRPα axis. The present inventors have found that a particular and singular domain within the extracellular region of human SIRPα binds CD47 with greater affinity than the intact extracellular region of human SIRPα. Also, it is demonstrated herein that in vivo efficacy of SIRPαFc fusions is surprisingly and dramatically improved when the constant (Fc) region is one having effector function, notwithstanding that inhibition of the CD47/SIRPα axis should require no such activity, and despite in vitro indications that an effectorless Fc region should be preferred.

The present SIRPαFc fusion proteins also demonstrate negligible CD47 agonism, permitting them to act as a dedicated inhibitor of SIRPα-mediated signalling in vivo. As a further attribute, the fusion protein exhibits negligible binding to red blood cells. This is in sharp contrast to other inhibitors of this axis, such as CD47 antibodies, that bind strongly to red blood cells, in some instances causing hemagglutination. With the present fusion protein, dosing does not need to account for the "sink" effect in which administered drug becomes sequestered and inactive in RBC-bound form, or to account for any adverse events caused by RBC interaction.

In one of its aspects, there is provided a SIRPαFc fusion protein useful to inhibit SIRPα-mediated stimulation of cell-bound CD47, the fusion protein comprising a SIRPα protein component and, fused therewith, an antibody constant region (Fc) component, wherein the SIRPα protein component consists of or comprises the V domain of human SIRPα and the Fc component is the constant region of an IgG having effector function. In embodiments, the Fc is selected from the constant region of an IgG1 antibody or an IgG4 antibody.

In a related aspect, there is provided a polynucleotide that encodes a secretable form of the SIRPαFc fusion as a single chain polypeptide. In another related aspect, there is provided a cellular host useful to produce the SIRPαFc fusion protein, the host having the polynucleotide incorporated expressibly therein. As well, in another embodiment, there is provided a method for obtaining the SIRPαFc fusion protein, comprising culturing or growing the host, and recovering the SIRPαFc fusion as a dimeric protein. In embodiments, the host is a eukaryotic host of any species that glycosylates expressed proteins.

In another of its aspects, the present invention provides a pharmaceutical composition useful to treat a subject presenting with a disease cell that is CD47+, the composition comprising a pharmaceutically acceptable carrier and an amount of the SIRPαFc fusion protein effective to inhibit the growth or proliferation of the CD47+ disease cell.

In a further aspect, the present invention provides a method for treating a subject presenting with CD47+ disease cells, the method comprising administering to the subject an amount of the SIRPαFc fusion protein effective to inhibit the growth and/or proliferation of the disease cells. In a related aspect, the present invention provides for the use of the SIRPαFc protein to treat cancer or any other disease in which CD47+ disease cells are present. There is also provided the use of the SIRPαFc protein for the manufacture of a medicament for the treatment of cancer or another disease in which CD47+ disease cells are present. Similarly, there is provided a pharmaceutical composition for use in treating a CD47+ disease cell, comprising the SIRPα-Fc protein and a pharmaceutically acceptable carrier. In embodiments, the disease cells are CD47+ cancer cells, particularly including CD47+ leukemia cells, such as AML.

These and other aspects of the present invention are now described in greater detail with reference to the accompanying drawings, in which:

REFERENCE TO THE FIGURES

FIG. 1 compares the binding of SIRPα fusions designated TTI-602 and TTI-616 to human CD47 using a direct binding assay (FIG. 1A) and an indirect competition assay (FIG. 1B). More particularly, the binding of SIRPαFc with a single N-terminal SIRPα V-domain (TTI-616) was compared to a fusion consisting of all three (V-C-C) extracellular SIRPα domains (TTI-602). A) Direct binding assay. CD47+ human Jurkat T cells were incubated with titrated amounts of TTI-602 or TTI-616 and binding analyzed by flow cytometry using a polyclonal anti-IgG antibody. B) Competitive inhibition assay. Jurkat cells were incubated with biotinylated SIRPαFc (TTI-601) in the presence of titrated amounts of cold competitor TTI-602 or TTI-616. Binding was measured by flow cytometry, and the results converted to percentage inhibition, with 0% defined as binding in the absence of competitor.

Figure 2:
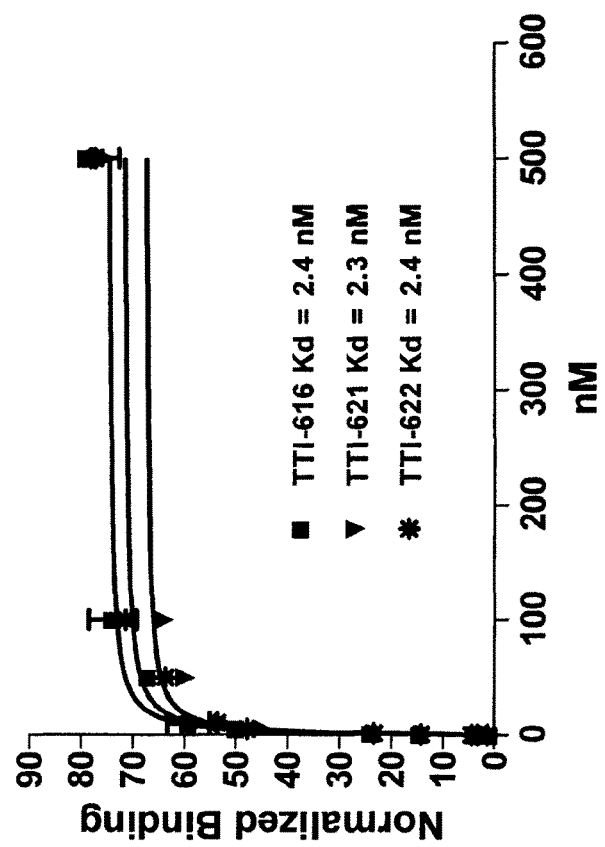

FIG. 2 shows binding profiles (Kd) for three different SIRPα fusion proteins. Revealed are very similar binding profiles, producing nearly identical affinity binding (Kd) values (2.3-2.4 nM). This was expected, as all three proteins contain the same SIRPα region and the Fc region was not predicted to affect ligand binding. More particularly, CD47+ human Jurkat T cells were incubated with titrated amounts of fusion proteins and binding analyzed by flow cytometry using a polyclonal anti-IgG antibody. The geometric means were then normalized and the binding curves and Kd values were generated by Prism (Graphpad) using nonlinear regression fitting the data to a one site binding model.

Figure 3:
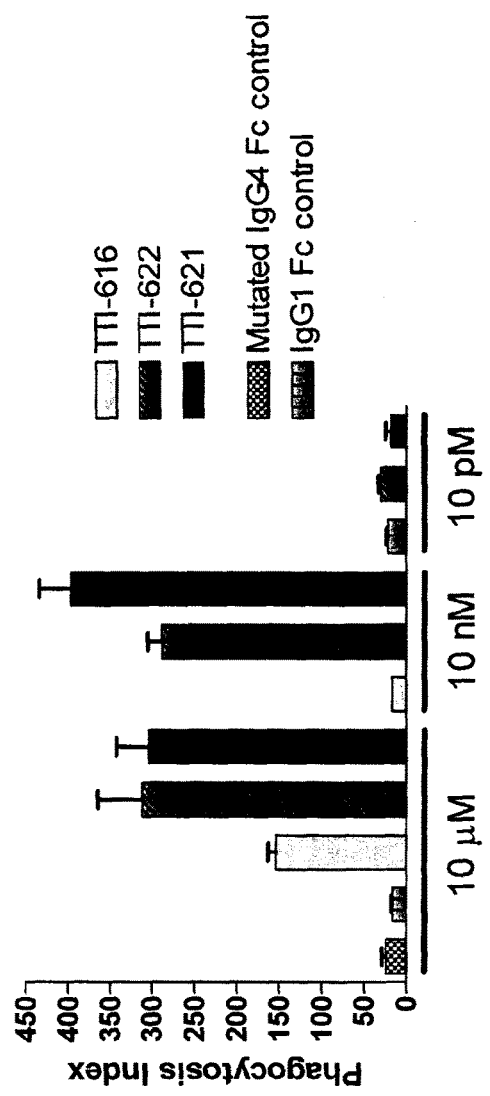

FIG. 3 (see also FIG. 6) shows that TTI-621 and TTI-622 exhibit similar pro-phagocytosis activity, whereas TTI-616 is clearly weaker (this is particularly evident at the 10 nM dose). This indicates either a wild type IgG4 or IgG1Fc region is required for maximal SIRPαFc-triggered tumor cell killing by macrophages. More particularly, macrophages were generated by culturing human peripheral blood CD14+ monocytes for at least 1 week in the presence of monocyte colony stimulating factor, and then activated with interferon-gamma (overnight) and LPS (1 hour). OCI/AML-2 cells were labeled with CFSE and incubated for 30 minutes with SIRPαFc fusions at the indicated concentrations or control Fc proteins (mutated hIgG4 Fc (TTI-401) or hIgG1 Fc (TTI-402)) at 1 mM or left untreated (UT). The AML-2 cells and macrophages were then co-cultured for 2 hours, and the macrophages were stained with wheat germ agglutinin Alexa Fluor® 555 conjugate and analyzed by confocal microscopy. The phagocytosis index is defined as the number of AML cells engulfed per 100 macrophages, counting at least 200 macrophages per sample. Fusion proteins with a mutated hIgG4 Fc region are shown as white bars, wild type hIgG4 as grey bars and wild type IgG1 as black bars. **$p<0.05$, *$p<0.01$ vs. isotype control (one-way ANOVA and Dunnett's post-test).

Figure 4:
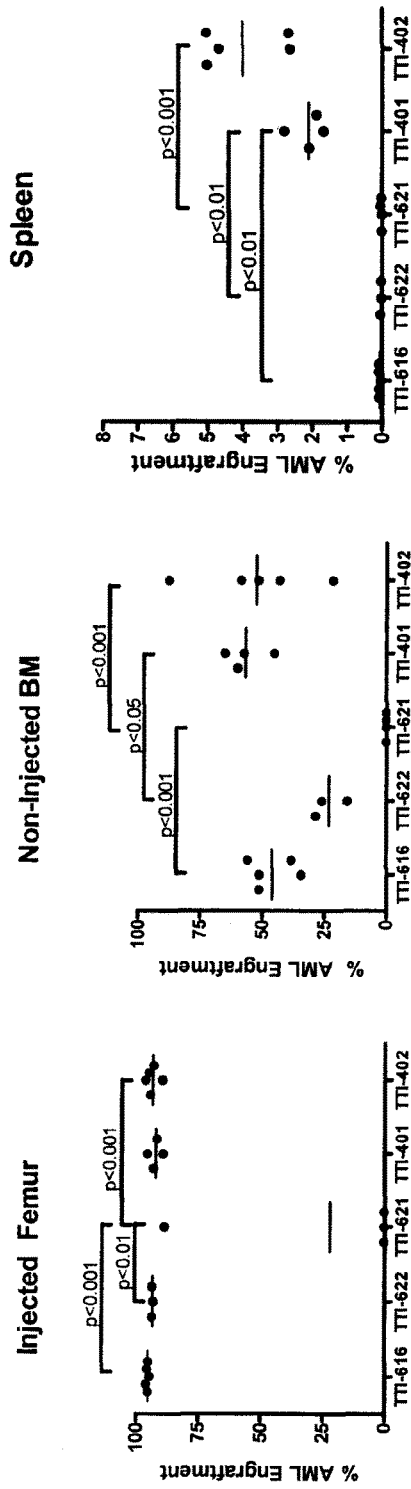

FIG. 4 shows that the TTI-621 fusion protein bearing an IgG1 Fc region was the only protein capable of mediating an anti-leukemic effect at the site of transplantation (the injected femur). In the non-injected bone marrow, there was a clear Fc dependent effect, with TTI-621 (full Fc activity) >TTI-622 (low Fc activity)>TTI-616 (no Fc activity). NOD/ShiLtJ-Prkdc$^{scid}$ (NOD.SCID) mice (8-12 weeks old) were sublethally irradiated with 275 cGy from a 137Cs g-irradiator and treated with anti-CD 122 antibody (to deplete NK cells) prior to intrafemoral injection of AML cells collected from a human leukemia patient. Starting three weeks after transplantation, mice were treated with SIRPαFc fusion proteins (8 mg/kg IP three times per week) or equimolar doses of control Fc proteins TTI-401 (mutated human IgG4) or TTI-402 (human IgG1). After 4 weeks of treatment, mice were sacrificed and human leukemia cells in the injected femur, non-injected bone marrow and spleen detected by flow cytometric analysis, staining for expression of human CD45 and human CD33 markers. The AML engraftment was expressed as the percentage of human CD45+CD33+ cells in each compartment.

Figure 5:
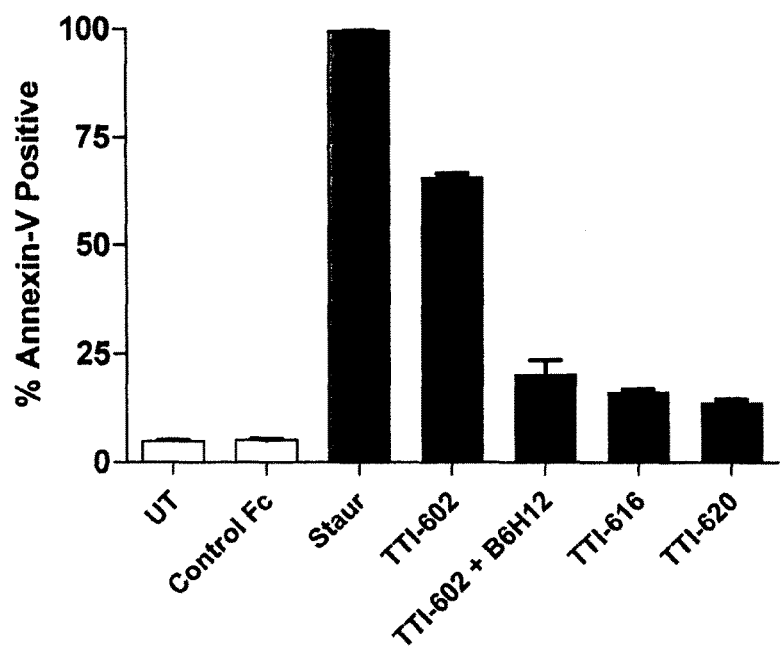

FIG. 5 CD47+ human Jurkat T cells were incubated with SIRPaFc fusion proteins or control Fe (3 μM) or left untreated (UT) overnight and then stained for Annexin-V and analyzed by flow cytometry. The pro-apoptotic agent staurosporine (Staur) at 1 μM was included as a positive control. One sample containing TTI-602 was pretreated with B6H12, a CD47-blocking antibody.

Figure 6:
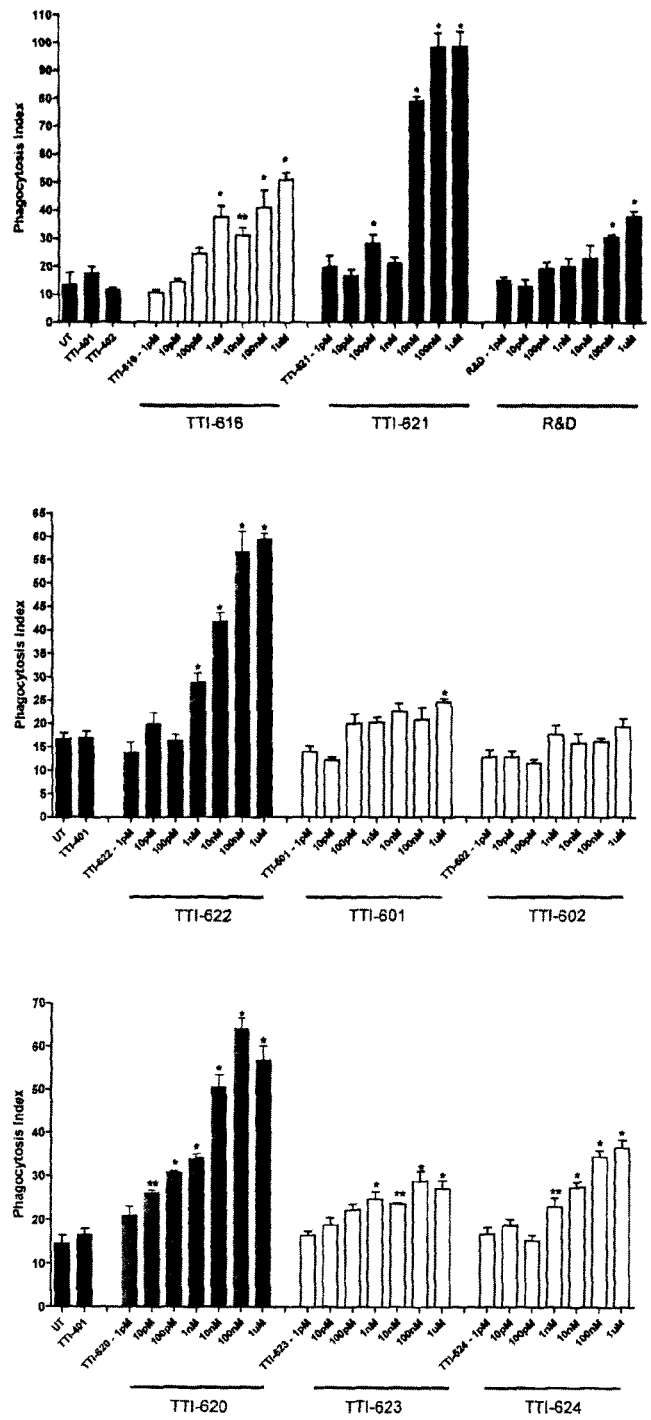

FIG. 6 shows results obtained using the protocols described for FIG. 3, but with a more developed data set.

Figure 7:
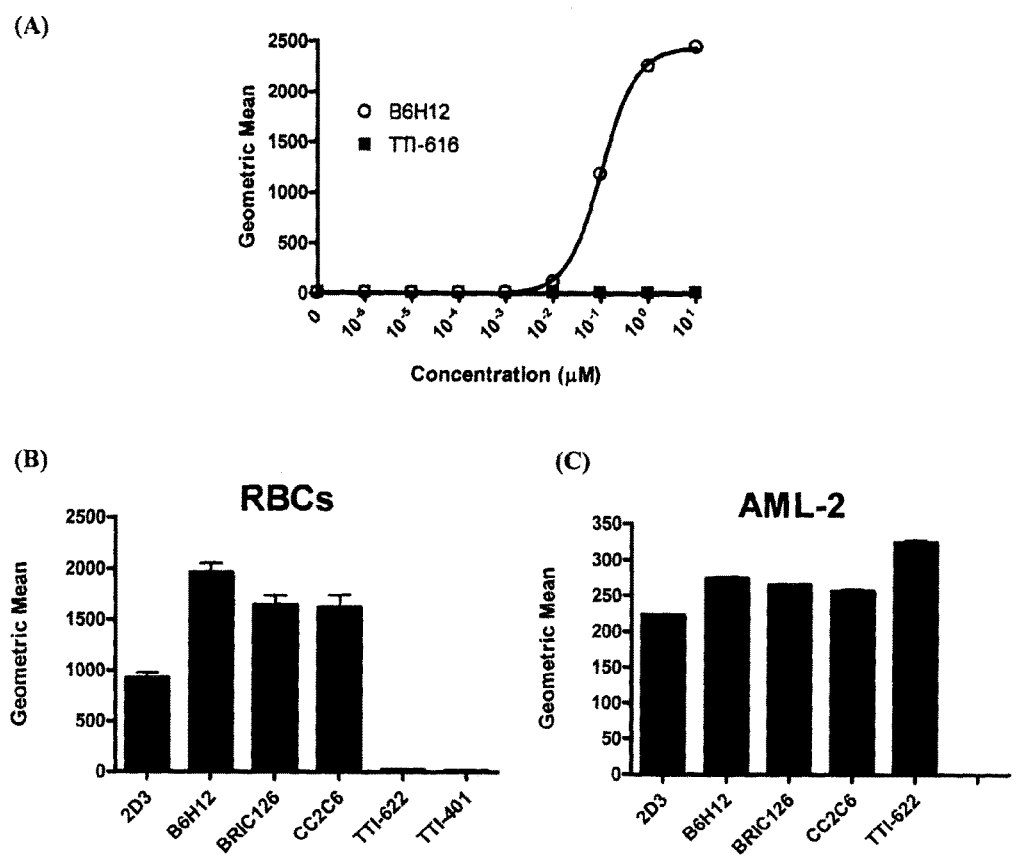

FIG. 7 A) Human erythrocytes were stained with titrated amounts of the anti-CD47 antibody B6H12 or TTI-616 and analyzed by flow cytometry. B) Human erythrocytes were stained with a panel of anti-CD47 monoclonals (2D3, B6H12, BRIC126 and CC2C6) or SIRPαFc fusion protein TTI-622 and analyzed by flow cytometry. Each reagent was used at a saturating concentration identified in previous optimization experiments. TTI-401 was used as a control Fc. Data shown are pooled from six donors. C) AML-2 tumor cells were stained with CD47 antibodies or TTI-622 and analyzed by flow cytometry. Data are shown for a single high dose (660 nM) of each reagent.

DETAILED DESCRIPTION OF THE INVENTION

The present invention relates to the human SIRPα protein, in a form fused directly or indirectly with an antibody constant region, or Fe. Unless otherwise stated, the term "human SIRPα" as used herein refers to a wild type, endogenous, mature form of human SIRPα. In humans, the SIRPα protein is found in two major forms. One form, the variant 1 or V1 form, has the amino acid sequence set out as NCBI RefSeq NP_542970.1 (residues 27-504 constitute the mature form). Another form, the variant 2 or V2 form, differs by 13 amino acids and has the amino acid sequence set out in GenBank as CAA71403.1 (residues 30-504 constitute the mature form). These two forms of SIRPα constitute about 80% of the forms of SIRPα present in humans, and both are embraced herein by the term "human SIRPα". Also embraced by the term "human SIRPα" are the minor forms thereof that are endogenous to humans and have the same property of triggering signal transduction through CD47 upon binding thereto. The present invention is directed most particularly to the variant 2 form, or V2.

The present SIRPαFc fusion proteins incorporate one of the three so-called immunoglobulin (Ig) domains that lie within the extracellular region of human SIRPα. More particularly, the present SIRPαFc proteins incorporate residues 32-137 of human SIRPα (a 106-mer), which constitute and define the IgV domain of the V2 form according to current nomenclature. This SIRPα sequence, shown below, is referenced herein as SEQ ID No.1.

[SEQ ID No. 1]
EELQVIQPDKSVSVAAGESAILHCTVTSLIPVGPIQWFRGAGPARELIYN

QKEGHFPRVTTVSESTKRENMDFSISISNITPADAGTYYCVKFRKGSPDT

EFKSGA

In a preferred embodiment, the SIRPαFc fusion proteins incorporate the IgV domain as defined by SEQ ID No.1, and additional, flanking residues contiguous within the SIRPα sequence. This preferred form of the IgV domain, represented by residues 31-148 of the V2 form of human SIRPα, is a 118-mer having SEQ ID No. 22 shown below:

[SEQ ID No. 22]
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPS

It has been found that the activity of this V2 form of human SIRPα is surprisingly greater, in terms of CD47 binding affinity, relative to the CD47 binding affinity of the entire extracellular domain of SIRPα. This binding affinity is at least two fold greater than the binding affinity of the entire extracellular domain. In embodiments, the affinity is at least 3 fold, 4 fold, 5 fold or greater for the V2 domain relative to the entire extracellular domain. In a direct binding assay, as reported in Example 1 herein, a fusion protein that incorporates this SIRPα domain has a binding affinity approximately 10-fold greater than a fusion protein that incorporates the entire SIRPα extracellular domain. Likewise, in an indirect competition assay also reported in Example 1 herein, the V2/IgV single-domain fusion provides a binding affinity that is superior to the CD47 binding affinity of a fusion that incorporates the entire extracellular region of SIRPα. Accordingly, SIRPαFc fusions based on this preferred V domain have the potential for greater potency in inhibiting the CD47 signalling that is stimulated upon binding with SIRPα.

The present SIRPα fusion proteins also incorporate an Fc region having effector function. The preference for effector function is entirely surprising, and difficult to explain with current information regarding the CD47/SIRPα axis. It could be expected that an effectorless Fc region would have activity sufficient to inhibit this axis, and that nothing more would be gained by integrating effector function. Nevertheless, the data herein as presented particularly in Example 5 show clearly that a benefit attaches to an effector-active Fc, in terms of the anti-leukemic in vivo activity of the fusion. This is particularly surprising in light of the results shown in Example 4, where the phagocytic activity of the fusion appears in vitro to show no particular preference for fusions based on either effector-active or effectorless Fc components.

For use in the present SIRPαFc fusion s, suitable Fc components thus are those having effector function. An Fc component "having effector function" is an Fc component having at least some effector function, such as at least some contribution to antibody-dependent cellular cytotoxicity or some ability to fix complement. Also, the Fc will at least bind to Fc receptors. These properties can be revealed using assays established for this purpose. Functional assays include the standard chromium release assay that detects target cell lysis. By this definition, an Fc region that is wild type IgG1 or IgG4 has effector function, whereas the Fc region of a human IgG4 mutated to eliminate effector function, such as by incorporation of an alteration series that includes Pro233, Val234, Ala235 and deletion of Gly236 (EU), is considered not to have effector function. In a preferred embodiment, the Fc is based on human antibodies of the IgG 1 isotype. The Fc region of these antibodies will be readily identifiable to those skilled in the art. In embodiments, the Fc region includes the lower hinge-CH2-CH3 domains.

In a specific embodiment, the Fc region is based on the amino acid sequence of a human IgG1 set out as P01857 in UniProtKB/Swiss-Prot, residues 104-330, and has the amino acid sequence shown below and referenced herein as SEQ ID No.2:

[SEQ ID No. 2]
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK*

Thus, in embodiments, the Fc region has either a wild type or consensus sequence of an IgG1 constant region. In alternative embodiments, the Fc region incorporated in the fusion protein is derived from any IgG1 antibody having a typical effector-active constant region. The sequences of such Fc regions can correspond, for example, with the Fc regions of any of the following IgG1 sequences (all referenced from GenBank), for example: BAG65283 (residues 242-473), BAC04226.1 (residues 247-478), BAC05014.1 (residues 240-471), CAC20454.1 (residues 99-320), BAC05016.1 (residues 238-469), BAC85350.1 (residues 243-474), BAC85529.1 (residues 244-475), and BAC85429.1 (residues (238-469).

In other embodiments, the Fc region has a sequence of a wild type human IgG4 constant region. In alternative embodiments, the Fc region incorporated in the fusion protein is derived from any IgG4 antibody having a constant region with effector activity that is present but, naturally, is significantly less potent than the IgG1 Fc region. The sequences of such Fc regions can correspond, for example, with the Fc regions of any of the following IgG4 sequences: P01861 (residues 99-327) from UniProtKB/Swiss-Prot and CAC20457.1 (residues 99-327) from GenBank.

In a specific embodiment, the Fc region is based on the amino acid sequence of a human IgG4 set out as P01861 in UniProtKB/Swiss-Prot, residues 99-327, and has the amino acid sequence shown below and referenced herein as SEQ ID No.23:

[SEQ ID No. 23]
ESKYGPPCPSCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK

In embodiments, the Fc region incorporates one or more alterations, usually not more than about 5 such alterations, including amino acid substitutions that affect certain Fc properties. In one specific and preferred embodiment, the Fc region incorporates an alteration at position 228 (EU numbering), in which the serine at this position is substituted by a proline ($S^{228}P$), thereby to stabilize the disulfide linkage within the Fc dimer. Other alterations within the Fc region can include substitutions that alter glycosylation, such as substitution of $Asn^{297}$ by glycine or alanine; half-life enhancing alterations such as $T^{252}L$, $T^{253}S$, and $T^{256}F$ as taught in U.S. 62/777,375, and many others. Particularly useful are those alterations that enhance Fc properties while remaining silent with respect to conformation, e.g., retaining Fc receptor binding.

In a specific embodiment, and in the case where the Fc component is an IgG4 Fc, the Fc incorporates at least the $S^{228}P$ mutation, and has the amino acid sequence set out below and referenced herein as SEQ ID No.24:

[SEQ ID No. 24]
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK

The present invention thus provides a fusion protein useful to inhibit the binding of human SIRPα and human CD47, thereby to inhibit or reduce transmission of the signal mediated via SIRPα-bound CD47, the fusion protein comprising a human SIRPα component and, fused therewith, an Fc component, wherein the SIRPα component comprises or consists of a single IgV domain of human SIRPα V2 and the Fc component is the constant region of a human IgG having effector function.

In one embodiment, the fusion protein comprises a SIRPα component consisting at least of residues 32-137 of the V2 form of wild type human SIRPα, i.e., SEQ ID No.1. In a preferred embodiment, the SIRPα component consists of residues 31-148 of the V2 form of human SIRPα, i.e., SEQ ID No.22. In another embodiment, the Fc component is the Fc component of the human IgG1 designated P01857, and in a specific embodiment has the amino acid sequence that incorporates the lower hinge-CH2-CH3 region thereof i.e., SEQ ID No.2.

In a preferred embodiment, therefore, the present invention provides a SIRPαFc fusion protein, as both an expressed single chain polypeptide and as a secreted dimeric fusion thereof, wherein the fusion protein incorporates a SIRPα component having SEQ ID No.1 and preferably SEQ ID No, 22 and, fused therewith, an Fc region having effector function and having SEQ ID No.2. When the SIRPα component is SEQ ID No. 1, this fusion protein comprises SEQ ID No.3, shown below:

[SEQ ID No. 3]
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPSDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK*

When the SIRPα component is SEQ ID No. 22, this fusion protein comprises SEQ ID No. 25, shown below:

[SEQ ID No. 25]
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPSDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

In alternative embodiments, the Fc component of the fusion protein is based on an IgG4, and preferably an IgG4 that incorporates the $S^{228}P$ mutation. In the case where the fusion protein incorporates the preferred SIRPα IgV domain of SEQ ID No.22, the resulting IgG4-based SIRPα-Fc protein has SEQ ID No. 26, shown below:

[SEQ ID No. 26]
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPSESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK

In preferred embodiments of the invention, the fusion protein comprises, as the SIRPα IgV domain of the fusion protein, a sequence that is SEQ ID No.22. The preferred SIRPα Fc is SEQ ID No.25.

In the SIRPαFc fusion protein, the SIRPα component and the Fc component are fused, either directly or indirectly, to provide a single chain polypeptide that is ultimately produced as a dimer in which the single chain polypeptides are coupled through intrachain disulfide bonds formed within the Fc region. The nature of the fusing region is not critical. The fusion may be direct between the two components, with the SIRP component constituting the N-terminal end of the fusion and the Fc component constituting the C-terminal end. Alternatively, the fusion may be indirect, through a linker comprised of one or more amino acids, desirably genetically encoded amino acids, such as two, three, four, five, six, seven, eight, nine or ten amino acids, or any number of amino acids between 5 and 100 amino acids, such as between 5 and 50, 5 and 30 or 5 and 20 amino acids. A linker may comprise a peptide that is encoded by DNA constituting a restriction site, such as a BamHI, ClaI, EcoRI, HindIII, PstI, SalI and XhoI site and the like.

The linker amino acids typically and desirably will provide some flexibility to allow the Fc and the SIRP components to adopt their active conformations. Residues that allow for such flexibility typically are Gly, Asn and Ser, so that virtually any combination of these residues (and particularly Gly and Ser) within a linker is likely to provide the desired linking effect. In one example, such a linker is based on the so-called $G_4S$ sequence (Gly-Gly-Gly-Gly-Ser) which may repeat as $(G_4S)_n$ where n is 1, 2, 3 or more, or is based on (Gly)n, (Ser)n, (Ser-Gly)n or (Gly-Ser)n and the like. In another embodiment, the linker is GTELSVRAKPS (SEQ ID No.21). This sequence constitutes SIRPα sequence that C-terminally flanks the IgV domain (it being understood that this flanking sequence could be considered either a linker or a different form of the IgV domain when coupled with the IgV minimal sequence described above). It is necessary only that the fusing region or linker permits the components to adopt their active conformations, and this can be achieved by any form of linker useful in the art.

The SIRPαFc fusion is useful to inhibit interaction between SIRPα and CD47, thereby to block signalling across this axis. Stimulation of SIRPα on macrophages by CD47 is known to inhibit macrophage-mediated phagocytosis by deactivating myosin-II and the contractile cytoskeletal activity involved in pulling a target into a macrophage. Activation of this cascade is therefore important for the survival of CD47+ disease cells, and blocking this pathway enables macrophages to eradicate the CD47+ disease cell population.

The term "CD47+" is used with reference to the phenotype of cells targeted for binding by the present polypeptides. Cells that are CD47+ can be identified by flow cytometry using CD47 antibody as the affinity ligand. CD47 antibodies that are labeled appropriately are available commercially for this use (for example, clone B6H12 is available from Santa Cruz Biotechnology). The cells examined for CD47 phenotype can include standard tumour biopsy samples including particularly blood samples taken from the subject suspected of harbouring endogenous CD47+ cancer cells. CD47 disease cells of particular interest as targets for therapy with the present fusion proteins are those that "over-express" CD47. These CD47+ cells typically are disease cells, and present CD47 at a density on their surface that exceeds the normal CD47 density for a cell of a given type. CD47 overexpression will vary across different cell types, but is meant herein to refer to any CD47 level that is determined, for instance by flow cytometry as exemplified herein or by immunostaining or by gene expression analysis or the like, to be greater than the level measurable on a counterpart cell having a CD47 phenotype that is normal for that cell type.

Accordingly, for therapeutic use, there is provided a pharmaceutical composition comprising a pharmaceutically acceptable carrier, and a therapeutically effective amount of the present SIRPαFc fusion protein. As used herein, "pharmaceutically acceptable carrier" means any and all solvents, dispersion media, coatings, antibacterial and antifungal agents, isotonic and absorption delaying agents, and the like that are physiologically compatible and useful in the art of protein/antibody formulation. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent. In embodiments, the SIRPαFc fusion is formulated using practises standard in the art of therapeutic antibody formulation. Solutions that are suitable for intravenous administration, such as by injection or infusion, are particularly useful.

Sterile injectable solutions can be prepared by incorporating the active compound in the required amount in an appropriate solvent with one or a combination of ingredients noted above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation are vacuum drying and freeze-drying (lyophilization) that yield a powder of the active ingredient plus any additional desired ingredient from a previously sterile-filtered solution thereof.

As used herein, "effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The SIRPαFc fusion protein may be administered to the subject through any of the routes established for protein delivery, in particular intravenous, intradermal and subcutaneous injection or infusion, or by oral or nasal administration. The fusion protein will typically be administered at a dose in the range 0.5 to 15 mg/kg body weight of the subject per day. It will be appreciated that the effective dose (an amount effective in treating the disease or condition, as evidenced by a reduction in the growth or rate of proliferation or size of the cancer cells or mass) will vary according to a number of factors including the age and general health of the subject and the severity of the disease to be treated.

The amount of active ingredient that can be combined with a carrier material to produce a single dosage form will vary depending upon the subject being treated, and the particular mode of administration. The amount of active ingredient required to produce a single, unit dosage form will generally be that amount of the composition that produces a therapeutic effect. Generally, out of one hundred percent, this amount will range from about 0.01 percent to about ninety-nine percent of active ingredient, preferably from about 0.1 percent to about 70 percent, e.g., from about 1 percent to about 30 percent of active ingredient in combination with a pharmaceutically acceptable carrier.

A composition of the present invention can be administered via one or more routes of administration using one or more of a variety of methods known in the art. As will be appreciated by the skilled artisan, the route and/or mode of administration will vary depending upon the desired results. Preferred routes of administration for fusion proteins of the invention include intravenous, intramuscular, intradermal, intraperitoneal, subcutaneous, spinal or other parenteral routes for administration, for example by injection or infusion. The phrase "parenteral administration" that include injection such as intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a fusion protein of the invention can be administered via a non-parenteral route, such as a by instillation or by a topical, epidermal or mucosal route of administration, for example, intranasally, orally, vaginally, rectally or sublingually.

Dosing regimens are adjusted to provide the optimum desired response (e.g., a therapeutic response). For example, a single bolus may be administered, or several divided doses may be administered over time or the dose may be proportionally reduced or increased as indicated by the therapeutic situation. It is especially advantageous to formulate parenteral compositions in dosage unit form for ease of administration and uniformity of dosage. "Unit dosage form" as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the fusion protein, the unit dose will be within the range from about 0.0001 to 100 mg/kg, and more usually 0.01 to 5 mg/kg, of the host body weight. For example dosages can be 0.3 mg/kg body weight, 1 mg/kb body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for the fusion protein of the invention include 1 mg/kg body weight or 3 mg/kg body weight via intravenous administration, with the fusion protein being given using one of the following dosing schedules; (i) every four weeks for six dosages, then every three months; (ii) every three weeks; (iii) 3 mg/kg body weight once followed by 1 mg/kg body weight every three weeks. In some methods, dosage is adjusted to achieve a plasma fusion protein concentration of about 1-1000 ug/ml and in some methods about 25-300 ug/ml.

The present fusion protein displays negligible binding to red blood cells. There is accordingly no need to account for an RBC "sink" when establishing effective dosing regimens. Relative to other SIRPα/CD47 inhibitors that are bound by RBCs, it is estimated that the present SIRP-Fc fusion can be effective at doses that are less than half the doses required for drugs that become RBC-bound, such as CD47 antibodies.

Moreover, the SIRPα-Fc fusion protein is a dedicated antagonist of the SIRPα-mediated signal, as it displays negligible CD47 agonism when binding thereto. There is accordingly no need, when establishing medically useful unit dosing regimens, to account for any stimulation induced by the drug.

The fusion protein can also be administered as a sustained release formulation, in which case less frequent administration is required. Dosage and frequency vary depending on the half-life of the fusion protein in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient show partial or complete amelioration of symptoms of disease. Thereafter, the patient can be treated using a prophylactic regimen.

The SIRPαFc proteins of the present invention are useful to treat a variety of CD47+ disease cells. These include particularly CD47+ cancer cells, including liquid and solid tumours. In one embodiment, the SIRPαFc proteins are used to inhibit the growth or proliferation of hematological cancers. As used herein, "hematological cancer" refers to a cancer of the blood, and includes leukemia, lymphoma and myeloma among others. "Leukemia" refers to a cancer of the blood, in which too many white blood cells that are ineffective in fighting infection are made, thus crowding out the other parts that make up the blood, such as platelets and red blood cells. It is understood that cases of leukemia are classified as acute or chronic. Certain forms of leukemia may be, by way of example, acute lymphocytic leukemia (ALL); acute myeloid leukemia (AML); chronic lymphocytic leukemia (CLL); chronic myelogenous leukemia (CML); myeloproliferative disorder/neoplasm (MPDS); and myelodysplastic syndrome. "Lymphoma" may refer to a Hodgkin's lymphoma, both indolent and aggressive non-Hodgkin's lymphoma, Burkitt's lymphoma, and follicular lymphoma (small cell and large cell), among others. Myeloma may refer to multiple myeloma (MM), giant cell myeloma, heavy-chain myeloma, and light chain or Bence-Jones myeloma.

In some embodiments, the hematological cancer treated with the SIRPαFc protein is a CD47+ leukemia, preferably selected from acute lymphocytic leukemia, acute myeloid leukemia, chronic lymphocytic leukemia, chronic myelogenous leukemia, and myelodysplastic syndrome, preferably, human acute myeloid leukemia.

In other embodiments, the hematological cancer treated with the SIRPαFc protein is a CD47+ lymphoma or myeloma selected from Hodgkin's lymphoma, both indolent and aggressive non-Hodgkin's lymphoma, Burkitt's lymphoma, follicular lymphoma (small cell and large cell), multiple myeloma (MM), giant cell myeloma, heavy-chain myeloma, and light chain or Bence-Jones myeloma as well as leimyosarcoma.

Solid tumours can also be treated with the present fusion protein, to reduce the size, number or growth rate thereof and to control growth of cancer stem cells. Such solid tumours include CD47+ tumours in bladder, brain, breast, lung, colon, ovaries, prostate, liver and other tissues as well.

The SIRPαFc protein can be administered alone, as monotherapy, or in combination with any other agent useful in the treatment of the targeted indication.

The SIRPαFc protein also is useful for detecting the presence of CD47+ cells. This can be achieved either indirectly, by first incubating the protein and test cells with the fusion protein and then probing with a detectable agent that binds the fusion protein, or directly by providing the fusion protein in labeled form.

In another aspect, the present invention features the fusion protein conjugated to a diagnostic or therapeutic moiety, such as a detectable marker, a cytotoxin, a drug or a radiotoxin. Conjugates that include one or more cytotoxins are referred to as "immunotoxins" or drug conjugates. A cytotoxin or cytotoxic agent includes any agent that is detrimental to (e.g., kills) cells. Examples include taxol, ethidium bromide, emetine, mitomycin, etoposide, vincristine, vinblastine, colchicine, doxorubicin, daunorubicin, mitoxantrone, mighramycin, and actinomycin D. Therapeutic agents also include, for example, antimetabolites (e.g., methotrexate, 6-mercaptopurine, 6-thioguanine, and cytarabine), alkylating agents (e.g., cyclophosphamide, busulfan, mitomycin C, and cisplatin), anthracyclines (e.g., daunorubicin and doxorubicin), and antibiotics (e.g., dactinomycin (formerly actinomycin), bleomycin, mithramycin, and anthramycin (AMC), and anti-mitotic agents (e.g., vincristine and vinblastine)

Non-limiting examples of detectable markers to which a fusion protein can be conjugated include fluorescein, cyanin, Cy-3, biotin, radioisotopes including I-$^{123}$ and I-$^{125}$, and the like. Fusion proteins can be labelled with such detectable markers by methods known in the art.

Cytotoxins can be conjugated to fusion proteins of the invention using linker technology available in the art. Examples of linker types that have been used to conjugate a cytotoxin to an fusion protein include, but are not limited to, hydrazones, thioethers, esters, disulfides and peptide-containing linkers.

Fusion proteins of the present invention also can be conjugated to a radioactive isotope to generate cytotoxic radiopharmaceuticals, also referred to as radioconjugates. Examples of radioactive isotopes that can be conjugated to fusion proteins for use diagnostically or therapeutically include, but are not limited to, iodine$^{131}$, indium$^{111}$, yttrium$^{90}$, and lutetium$^{177}$. Methods for preparing radioconjugates are established in the art.

In one embodiment, the fusion proteins can be used to detect levels of CD47, or levels of cells that contain CD47 on their membrane surface. Detection of CD47 using a SIRPαFc fusion protein can be achieved, for example, by contacting a sample (such as an in vitro sample) and a control sample with the fusion protein under conditions that allow for the formation of a complex between the fusion protein and CD47. Any complexes formed between the fusion protein and CD47 are detected and compared in the sample and the control. For example standard detection methods, well-known in the art, such as ELISA and flow cytometric assays, can be performed using the compositions of the invention.

The fusion proteins thus are useful for diagnostic purposes, including sample testing and in vivo imaging, and for therapeutic purposes to treat diseases having, as one hallmark, disease cells in which CD47 is upregulated.

For either purpose, the fusion protein can be conjugated to an appropriate agent, to form a drug conjugate. Agents appropriate for treating disease include cytotoxic agents such as chemotherapeutics and radiotherapeutics. For diagnostic purposes, appropriate agents are detectable labels that include radioisotopes, for whole body imaging, and radioisotopes, enzymes, fluorescent labels and other suitable antibody tags for sample testing.

For CD47 detection, the detectable labels can be any of the various types used currently in the field of in vitro diagnostics, including particulate labels including metal sols such as colloidal gold, isotopes such as I$^{125}$ or Tc$^{99}$ presented for instance with a peptidic chelating agent of the N2S2, N3S or N4 type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3, 2'-(5'-chloro)tricyclo{3.3.1.1 3,7}decan}-4-yl)phenyl phosphate (CSPD), as well as CDP and CDP-star® or other luminescent substrates well-known to those in the art, for example the chelates of suitable lanthanides such as Terbium (III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

For SIRPαFc fusion protein-based therapy, the cytotoxin may be conjugated with the fusion protein through non-covalent interaction, but more desirably, are coupled by covalent linkage either directly or, more preferably, through a suitable linker. In a preferred embodiment, the conjugate comprises a cytotoxin and a fusion protein. Conjugates of the fusion protein and cytotoxin are made using a variety of bifunctional protein coupling agents such as N-succinimidyl-3-(2-pyridyldithiol)propionate, iminothiolane, bifunctional derivatives of imidoesters such as dimethyl adipimidate HCl, active esters such as disuccinimidyl suberate, aldehydes such as glutaraldehyde, bis-azido compounds such as bis-(p-diazoniumbenzoyl)-ethylenediamine), diisocyanates such as toluene 2,6-diisocyanate, and bis-active fluorine compounds (such as 1,5-difluoro-2,4-dinitrobenzene). C$^{14}$-labeled 1-isothiocyanobenzyl-3-methyldiethylene triaminepentaacetic acid (MX-DTPA) is a chelating agent suitable for conjugation of radionuclide to the antibody.

The cytotoxin component of the immunoconjugate can be a chemotherapeutic agent, a therapeutic antibody, a toxin such as an enzymatically active toxin of bacterial, fungal, plant or animal origin, or fragments thereof, or a small molecule toxin, or a radioactive isotope such as $^{212}$Bi, $^{131}$I, $^{131}$In, $^{111}$In, $^{90}$Y, and $^{186}$Re, or any other agent that acts to inhibit the growth or proliferation of a cancer cell.

Chemotherapeutic agents useful in the generation of such drug conjugates include the maytansinoids including DM-1 and DM-4, auristatins, adriamycin, doxorubicin, epirubicin, 5-fluorouracil, cytosine arabinoside ("Ara-C"), cyclophosphamide, thiotepa, busulfan, cytoxin, taxoids, e.g. paclitaxel, and docetaxel, taxotere, methotrexate, cisplatin, melphalan, vinblastine, bleomycin, etoposide, ifosamide, mitomycin C, mitoxantrone, vincristine, vinorelbine, carboplatin, teniposide, daunomycin, carminomycin, aminopterin, dactinomycin, mitomycins, esperamicins, 5-FU, 6-thioguanine, 6-mercaptopurine, actinomycin D, VP-16, chlorambucil, melphalan, and other related nitrogen mustards. Also included are hormonal agents that act to regulate or inhibit hormone action on tumors such as tamoxifen and onapristone. Toxins and fragments thereof which can be used include diphtheria A chain, nonbonding active fragments of diphtheria toxin, cholera toxin, botulinus toxin, exotoxin A chain (from *Pseudomonas aeruginosa*), ricin A chain, abrin A chain, modeccin A chain, alpha-sarcin, *Aleurites fordii* proteins, dianthin proteins, phytolaca Americana proteins (PAPI, PAPII, and PAP-S), *Momordica charantia* inhibitor, curcin, crotin, sapaonaria, officinalis inhibitor, gelonin, saporin, mitogellin, restrictocin, phenomycin, enomycin, and the tricothcenes. Small molecule toxins include, for example, calicheamicins, maytansinoids, palytoxin and CC1065.

Fusion proteins bind selectively to the target antigen, CD47, and are used, in accordance with an aspect of the invention, to screen cancer and other disease cells to detect those which present the CD47 antigen at high density. In a preferred embodiment, screening is applied to a sample of cancer cells taken from a subject that is a candidate for SIRPαFc fusion protein therapy. Subjects testing positive for cancer cells that present the CD47 antigen at high density can then be scheduled for therapy with the present fusion protein, or a conjugate hybrid thereof. Standard techniques, combined with the fusion proteins herein described can be used to screen cancer cells. Desirably, the fusion protein incorporates a detectable label. The label may be detectable by itself. (e.g., radio-isotope labels or fluorescent labels) or, in the case of an enzymatic label, may catalyze chemical alteration of a substrate compound or composition which is detectable. Radionuclides that can serve as detectable labels include, for example, I-$^{131}$, I-$^{123}$, I-$^{125}$, Y-$^{90}$, Re-$^{188}$, Re-$^{186}$, At-$^{211}$, Cu-$^{67}$, Bi-$^{212}$, and Pd-$^{109}$.

In situ detection of the binding to CD47+ cancer cells can be performed, using the present antibody or fragment, by immunofluorescence or immunoelectron microscopy. For this purpose, a histological specimen is removed from the patient, and a labeled form of the fusion protein is applied to it, preferably by overlaying the antibody on a biological sample. This procedure also allows for distribution of the CD47 antigen to be examined within biopsied tumour tissue. It will be apparent for those skilled in the art that a wide variety of histological methods are readily available for in situ detection.

More particularly, SIRPαFc fusion proteins of the present invention may be used to monitor the presence or absence of fusion protein reactivity in a biological sample (e.g., a tissue biopsy, a cell, or fluid) using standard detection assays. Immunological assays may involve direct detection, and are particularly suited for screening large amounts of samples for the presence of cancer cells that are CD47+. For example, the fusion protein can be used in the role of any antibody in any standard immunoassay format (e.g., ELISA, Western blot, immunoprecipitation, flow cytometry or RIA assay) to measure complex formation. Any appropriate label which may be directly or indirectly visualized may be utilized in these detection assays including, without limitation, any radioactive, fluorescent, chromogenic (e.g., alkaline phosphatase or horseradish peroxidase), or chemiluminescent label, or hapten (for example, digoxigenin or biotin) which may be visualized using a labeled, hapten-specific antibody or other binding partner (e.g., avidin). Exemplary immunoassays are described, e.g., in Ausubel et al., supra, Harlow and Lane, Antibodies: A Laboratory Approach, Cold Spring Harbor Laboratory, New York (1988), and Moynagh and Schimmel, Nature 400:105, 1999. For example, using the fusion proteins described herein, high density CD47 is readily detected at the cell surface using standard flow cytometry methods. Samples found to contain labeled complex compared to appropriate control samples are taken as indicating the presence of high density CD47, and are thus indicative of a cancer or other disease amenable to treatment with the present fusion proteins.

It will be appreciated that the present fusion proteins comprise two molecules, each comprising a single chain polypeptide that incorporates a SIRPα protein component fused to an Fc component.

Fusion of the single chain polypeptides to form a dimer results from disulfide bridges that form between the Fc components when the single chain polypeptides are secreted from the host cell producing them. Thus, the product recovered as a fusion protein is a dimeric protein resulting from the disulfide linkage between two molecules of the single chain polypeptide incorporating both the Fc component and the SIRPα component.

The present invention thus provides not only the single chain polypeptides in which the SIRPα protein component is fused with the Fc region, i.e., the CH component, but also provides a dimeric fusion protein in which two copies of these single chain polypeptides are fused via their respective Fc components. Multimeric forms, in which more than two copies of each polypeptide are fused, are also within the scope of the invention.

To produce the present SIRPαFc fusion proteins, DNA encoding a secretable form of the single chain polypeptide is obtained, incorporated within a suitable expression/secretion vector, and then transfected into a suitable production host. Culturing of the resulting transfectant yields the dimeric fusion protein as a secreted product which can then be harvested and purified, all in general accordance with established practise, and as exemplified herein. A polypeptide in single chain form can be obtained similarly, but is produced without the aid of a secretion signal and in a host such as a prokaryote so that dimerization does not occur and the polypeptide is recoverable as an intracellular protein.

Accordingly, the present invention also provides polynucleotides, including DNA and RNA, which upon expression yield a secretable form of the single chain polypeptides that make up the present fusion proteins. A polynucleotide encoding a preferred and secretable single chain polypeptide comprises the DNA sequence having SEQ ID No.8, in which the first 90 residues encode the 30-mer secretion signal native to human SIRPα, and the remaining nucleic acid residues (SEQ ID No. 7) encode the single chain FSIRPαFc polypeptide. Embodiments include polynucleotides in which one or more codons are substituted by codons synonymous with those illustrated.

In related embodiments, there is provided a polynucleotide that encodes a secretable form of the IgG1-based fusion protein having SEQ ID No. 25, the polynucleotide comprising SEQ ID No.27. Also provided is a polynucleotide that encodes a secretable form of the IgG4-based fusion protein having SEQ ID No. 26, the polynucleotide comprising SEQ ID No.28.

It will be appreciated that the polynucleotides can be synthesized de novo, using standard gene synthesis and cloning and amplification techniques to assemble the intact polynucleotides. Alternatively, and for example, a polynucleotide encoding the SIRPα protein component (e.g., SEQ ID No. 5) and a polynucleotide encoding the selected Fc component (e.g., SEQ ID No. 6) can be obtained by PCR amplification from publicly available sources of these genes, and the amplified polynucleotides can be linked by ligation, either directly or through a linker that encodes one or more amino acid residues innocuous in terms of biological activity, all in accordance with established techniques, and as exemplified herein.

For expression, a polynucleotide encoding the single chain polypeptide in secretable form is incorporated within vectors such as plasmids suitable for expressing the polynucleotides in the chosen fusion protein production host. Such vectors are available commercially, and typically are constructed to permit introduction of the polynucleotide encoding the secretable fusion protein directly under the control of a promoter effective to drive expression in the chosen host. Host transfection procedures are well established in the art, and expression systems that include vectors, and expression hosts for such vectors, are available commercially. These include the pcDNA vectors suitable for cotransfection into hosts 293, CHO or NSO, to express the fusion protein-encoding polynucleotides under control of the CMV promoter, available from Invitrogen, and the pTandem-1 vector system for expressing fusion protein chains under the CMV promoter and from bicistronic RNA in 293, CHO or NSO hosts, also available from Invitrogen. Another useful expression system, described in the examples herein, makes use of the CMV promoter and is available commercially from the Biotechnology Research Institute in Montreal, Canada.

Suitable production hosts for the fusion proteins of the invention are cells that incorporate, either transiently or stably, a polynucleotide encoding the fusion-forming single chain polypeptide in secretable form. The expressed form of the fusion protein incorporates a signal sequence enabling the secretion of each fusion protein chain from the host, thereby to permit the formation of desired disulfide linkages within and across the produced fusion protein chains, and provide a functional fusion protein. The secretion signal can be encoded by any such signal functional in the chosen host. In one embodiment, the secretion signal is the secretion signal normally associated with the SIRPα protein component.

Suitable mammalian host cells for expressing the recombinant fusion proteins of the invention include Chinese Hamster Ovary (CHO cells, including dhfr-CHO cells and CHOcTA cells), NSO myeloma cells, SOS cells and SP2 cells. In a specific embodiment, the host is a CHO cell line, such as a CHO-S cell line. For use with NSO myeloma cells, another preferred expression system is the GS gene expression system disclosed in WO 87/04462, WO 89/01036 and EP 338,841. The fusion proteins are produced by culturing the transfected host cells for a period of time sufficient to allow for secretion of the fusion protein into the culture medium in which the host cells are grown. Fusion proteins can recovered from the culture medium using standard protein purification methods, all as now exemplified.

EXAMPLES

In the description of the work that follows, reference is made to fusion proteins by code. For convenience, the functional components of the referenced fusions are summarized below:

TABLE 1

| Protein | SIRPα Region | Fc Region | Fc Effector Activity |
|---|---|---|---|
| TTI-601 | hSIRPα V1, 3 domains (340 aa) | hIgG4 (mut) | None |
| TTI-602 | hSIRPα V2, 3 domains (339 aa) | hIgG4 (mut) | None |
| TTI-616 | hSIRPα V2, 1 domain (118 aa) | hIgG4 (mut) | None |
| TTI-620 | hSIRPα V2, 1 domain (114 aa) | hIgG4 (WT)* | Low |
| TTI-621 | hSIRPα V2, 1 domain (118 aa) | hIgG1 (WT) | High |
| TTI-622 | hSIRPα V2, 1 domain (118 aa) | hIgG4 (WT) | Low |
| TTI-623 | hSIRPα V2, 1 domain (118 aa) FD6 mutations^ | hIgG4 (mut) | None |
| TTI-624 | hSIRPα V2, 1 domain (118 aa) CV1 mutations^ | hIgG4 (mut) | None |
| R&D** | hSIRPα V1, 3 domains (339 aa) | hIgG1 (WT) | High |

All human IgG4 Fc regions possess the hinge-stabilizing $S^{228}P$ mutation, except where indicated with an asterisk (*).
IgG4 Fcs designated as "mut" contain mutations at positions 233-236 (EU numbering system) that further reduce FcγR binding (Armour et al. 1999 *Eur. J. Immunol.* 29: 2613).
^FD6 mutations (L4V, V6I, A27I, I31F, E47V, K53R, E54Q, H56P, V63I, L66T, K68R, V92I) and CV1 mutations (V6I, A27I, I31F, E47V, K53R, E54Q, H56P, L66T, V92I) described in Weiskopf et al. 2013 *Science* 341: 88.
**Commercially available protein sold by R&D Systems (Cat #4546-SA-050).

1. SIRPα-Fc Fusion Protein Production

The SIRPαFc constructs were generated by a three-stage cloning process, using the primers shown below:

```
                                              SEQ ID No. 9
P#5863:  GGCGCTAGCCACCATGGAGC

SEQ ID No. 10
P#5929:  GGTGAAGCTCACTGTGTGCTG

SEQ ID No. 11
P#5930:  CAGCACACAGTGAGCTTCACC

SEQ ID No. 12
P#1035:  CCGGATCCTCATTTACCCAG

SEQ ID No. 13
P#0874:  GGACTCAGAGGGTTTGGCACGCACAGA

SEQ ID No. 14
P#0875:  CCCTCTGAGTCCAAATATGGTCCCCCA

SEQ ID No. 15
P#4197:  AGTTTTGTCAGAGGGTTTGGCACGCACAGA

SEQ ID No. 16
P#4198:  AAACCCTCTGACAAAACTCACACATGCCCA

SEQ ID No. 17
P#1737:  CACGGATCCTCATTTACCCGG

SEQ ID No. 18
P#4195:  AGGTGCTGGGCATGGTGGGCATGGGGG

SEQ ID No. 19
P#4196:  CCCCCATGCCCACCATGCCCAGCACCT

SEQ ID No. 20
P#2058:  CACGGATCCTCATTTACCCAGAGACAGGG
```

In the first PCR reaction, 100 ng of template DNA (synthetic human SIRPα GenBank #AAH26692, from Blue Heron Biotechnology) was amplified using platinum Pfx DNA polymerase (Invitrogen) in 1 mM MgSO$_4$, 0.4 mM each dNTP and 20 pmol of each primer, according to the conditions below:

TTI-602: primers P #5863 and P #5929; initial melting at 94° C. for 5 min, followed by 30 cycles consisting of 94° C. for 1 min, 56° C. for 2 min, and 68° C. for 2 min.

TTI-616: primers P #5863 and P #0874; initial melting at 94° C. for 5 min, followed by 30 cycles consisting of 94° C. for 1 min, 50° C. for 1.5 min, and 63° C. for 3 min.

TTI-621: primers P #5863 and P #4197; initial melting at 94° C. for 5 min, followed by 30 cycles consisting of 94° C. for 0.5 min, 50° C. for 1.5 min, and 63° C. for 3 min.

TTI-622: primers P #5863 and P #4195; initial melting at 94° C. for 5 min, followed by 30 cycles consisting of 94° C. for 0.5 min, 50° C. for 1.5 min, and 63° C. for 3 min.

The reactions were then held at 72° C. for 10 min and cooled to 4° C. The reaction products were electrophoresed through 1-1.4% agarose gels and visualized with ethidium bromide.

Next, the IgG Fc fragments were amplified in reaction PCR2, using Pfx DNA polymerase (Invitrogen), in 1 mM MgSO$_4$, 0.4 mM each dNTP, 20 pmol of each primer and 100 ng of template DNA (human IgG1 and human IgG4, previously cloned) under the following conditions:

TTI-602: primers P #5930 and P #1035; initial melting at 94° C. for 5 min, followed by 30 cycles consisting of 94° C. for 1 min, 56° C. for 2 min, and 72° C. for 2 min.

TTI-616: primers P #0875 and P #1035; initial melting at 94° C. for 5 min, followed by 30 cycles consisting of 94° C. for 1 min, 50° C. for 1.5 min, and 63° C. for 3 min.

TTI-621: primers P #4198 and P #1737; initial melting at 94° C. for 5 min, followed by 30 cycles consisting of 94° C. for 0.5 min, 60° C. for 0.5 min, and 68° C. for 0.5 min.

TTI-622: primers P #4196 and P #2058; initial melting at 94° C. for 5 min, followed by 30 cycles consisting of 94° C. for 0.5 min, 50° C. for 1.5 min, and 63° C. for 3 min.

The reactions were then held at 72° C. for 10 min and cooled to 4° C. The reaction products were electrophoresed through 1-1.4% agarose gels and visualized with ethidium bromide.

Finally, the SIRPα and Fc cDNA was assembled by overlapping PCR in reaction PCR3. Products from PCR1 and PCR2 (100 ng) were incubated with platinum Pfx DNA polymerase (Invitrogen), in 1 mM MgSO$_4$, and 0.4-0.8 mM each dNTP at 94° C. for 5 min, followed by 10 cycles consisting of 94° C. for 30 sec-1 min, then 52-60° C. for 80 sec-3 min, and cooled to 4° C. Primers (20-40 pmol each) were then added to first reaction and a second-stage reaction run under the following conditions: melting at 94° C. for 5 min, followed by 30 cycles consisting of 94° C. for 30 sec-1 min, 50-56° C. for 30 sec-3 min and 30 sec. The details of each condition are below:

TTI-602: 10 cycles at 94° C. for 1 min and 56° C. for 3 min, followed by 30 cycles of 94° C. for 1 min, 55° C. for 2.5 min, and 72° C. for 3 min using primers P #5863 and P #1035.

TTI-616: No first PCR cycle; 30 cycles of 94° C. for 1 min, 50° C. for 2 min, and 63° C. for 3.5 min using primers P #5863 and P #1035.

TTI-621: 10 cycles at 94° C. for 1 min and 52° C. for 3 min, followed by 30 cycles of 94° C. for 1 min, 52° C. for 2 min, and 63° C. for 4 min using primers P #5863 and P #1737.

TTI-622: 10 cycles at 94° C. for 1 min and 60° C. for 3 min, followed by 30 cycles of 94° C. for 1 min, 52° C. for 2 min, and 63° C. for 4 min using primers P #5863 and P #2058.

The reactions were then held at 68-72° C. for 7-8 min and cooled to 4° C. The reaction products were separated through 1-1.4% agarose gels and visualized with ethidium bromide and ligated into the pMPG expression vector (Biotechnology Research Institute in Montreal, Canada) as follows: The DNA band of interest from PCR amplification was excised and purified from agarose gel by using QIAquick Gel Extraction Kit (Qiagen). This purified PCR product was digested with NheI and BamHI restriction enzymes (New England BioLabs) and purified from gel using the Qiaquick gel Purification Kit (Qiagen). The fragment was then ligated by T4 DNA ligase (Invitrogen) into the pMPG expression plasmid that had been similarly digested with NheI and BamHI enzymes. The pMPG plasmid uses a CMV promoter and TK Poly A terminator and contains hygromycin resistance selection marker. 2 μl of the ligation reaction was then transformed into 25 μl of competent E. coli DH5α cells (Invitrogen) according the manufacturer instructions. Transformants were spread on LB-agar plates containing 100 μg/ml ampicillin (Sigma), followed by incubation at 37° C. for 20 hours. Plasmid DNA was extracted and purified from small-scale E. coli cultures by using the QIAprep Spin mini-prep Kit (Qiagen), and the DNA sequence was confirmed by automated sequencing using fluorescent dye-conjugated ddNTPs (Core Molecular Biology Facility, York University). For transfections, large quantities of plasmid DNA were prepared using the EndoFree Plasmid Maxi kit (Qiagen), then the sequence reconfirmed by automated sequencing using fluorescent dye-conjugated ddNTPs (Core Molecular Biology Facility, York University).

Cell Line Production

Stable transfectants were generated using CHO-S cell line (Invitrogen). Briefly, plasmid DNA isolated was linearized by XbaI (New England BioLabs), and purified using QIAGEN columns (Qiagen). CHO-S cells growing in serum-free chemical defined medium (CD-CHO, Invitrogen) supplemented with 8 mM L-glutamine and 1× HT-supplement were transfected with the linearized plasmid using Lipofectamine 2000 reagent (Invitrogen). After 48 hours, the cells were transferred into 96-well plates and plated out at different concentrations (10000, 5000, or 2000 cells/well) in medium containing 600 μg/mL of hygromycin B (Invitrogen). Mock transfection control was carried out in identical fashion with no DNA added to the mix. 2-3 weeks following transfection a panel of drug-resistant oligoclones was picked up and the supernatants from a 48 hr expression study were screened by ELISA as follows: 96-well plates were coated with 0.1 μg/well of capture Ab (goat anti-human IgGFc), and incubated overnight at 4° C. The wells were washed and blocked with 200 μl of 2% BSA in PBST at room temperature for 1 hour. After washing, 100 μl samples were diluted with 1% BSA in PBST, added to the wells, incubated for 1 hour, washed and then incubated with HRP-conjugated detection Ab (HRP-conjugated goat anti-human IgGFc), for 1 hour at room temperature. The wells were then washed and TMB substrate (Moss Inc.) added and incubated for 3 to 5 min at room temperature. Absorbance was measured at 450 nm/655 nm wavelength using iMark microplate reader (Biorad), and a standard curve was constructed using known amount of purified fusion protein. A second limiting dilution of the 3 highest expressing oligo-clones was performed at lower cell concentrations (0.1, 0.25, and 0.5 cells/well) in complete CD-CHO medium containing 600 μg/ml of hygromycin B. After 2 to 3 weeks, the drug-resistant clones were again assessed for recombinant protein production by ELISA as described above. The productivity was expressed in pg/cell/day and was in the range of 1.4-23.9 pg/cell/day for the human SIRPα fusion proteins. The highest expressing single cell clones were used for supernatant batch production in a WAVE Bioreactor system. In some instances before the single clone stage was reached, the best oligo clone was used for production.

Protein Purification

For rapid production of small lots of proteins, some SIRPα-Fc batches were made in transiently transfected 293F cells. Briefly, FreeStyle 293F cells (Invitrogen) were grown in 293F medium (Invitrogen), transfected with non-linearized plasmid DNA and 293Fectin reagent (Invitrogen) and grown in shaker flask batches in volumes 80-100 mL/flask at 37° C., 5% $CO_2$ for 3-6 days. Cell density and viability were monitored every day until cell viability dropped to ~90%. Cell viability at batch harvest was in the range 85-90%.

For purification from CHO-S cells, 5 or 10 L culture supernatant was generated from stably transfected high expressing oligo or single cell clones in a WAVE disposable bag bioreactor system Base20/50 EHT (GE Healthcare). Briefly, CHO-S transfectants were grown in static T150 flasks in completed growth medium (CD-CHO supplemented with 8 mM L-glutamine, 1× HT-supplement, and 600 μg/mL of hygromycin B) at 37° C. to produce sufficient cell numbers to initiate a 1 L or a 2 L culture at $0.5 \times 10^6$ cells/mL for a 5 L or a 10 L run respectively. The bioreactor bag was inoculated and the cells were then incubated at 37° C., 10% $CO_2$, rocking speed 15-20 rpm, angle 7°, and air flow 0.2-0.4 Lpm. When the culture reached a density of 2 to $2.5 \times 10^6$ cells/mL (usually within 2-3 days of inoculation), the bioreactor was further scaled up to 5 L or 10 L and incubated further at 37° C., 10% $CO_2$, rocking speed 15-20, angle 7°, air flow 0.2-0.4 Lpm. When the cells have reached a density of $1-1.5 \times 10^6$ cells/mL the temperature was dropped to 30° C. and culture was further incubated for additional 7 to 10 days at the conditions specified above. Starting on day 0 at 30° C. the cultures were fed with 1% CHO feed bioreactor supplement (Sigma) every two days and were harvested when the cell viability dropped around 90%. The supernatant was collected, centrifuged at 3000×g for 40 min at 4° C. and frozen at −20° C. until purification.

All proteins were purified by a two-step procedure, first using protein A chromatography. Buffer exchanged supernatant was diluted 9-fold with binding buffer (20 mM Na—P & 3 M NaCl, pH 7.8) and loaded onto a rProtein A column (GE Healthcare) at a flow rate of 2-3 mL/min (depending on loading volume and loading time) overnight at 4° C. The column was then washed with binding buffer (20 volumes at 3 mL/min), and protein eluted with 0.1 M citric acid pH 4.0 and pH 2.2 at 3 mL/min. Eluted material was pH adjusted to neutral with 1M and subsequently purified using HiTrap Phenyl HP chromatograph. Briefly, proteins were diluted at least 4-fold to 0.2 M ammonium sulphate pH 7.5 and loaded onto the HiTrap Phenyl HP column (GE Healthcare) at 2-3 mL/min (depending on column size and loading time). Non-aggregated SIRPαFc protein was collected in the flow-through fraction. Tangential flow filtration using a BioMax 10 membrane (Millipore) was used to concentrate and buffer exchange the protein into PBS pH 7.4. The quality of each protein was determined by SDS-PAGE, Western blot using goat anti-IgGFc antibody and rabbit anti-goat IgG HRP conjugate, and HPLC analysis. The identity of all proteins was confirmed by N-terminal sequencing and mass spectrometry.

1. Comparison of One and Three Domain SIRPαFc Fusions

SIRPα consists of three extracellular immunoglobulin (Ig)-like domains, however binding to CD47 is localized to the N-terminal domain. To determine the optimal SIRPα region for SIRPαFc fusions, we generated proteins incorporating either all three extracellular SIRPα domains (TTI-602) or the single N-terminal domain (TTI-616).

Both proteins were constructed on a mutated human IgG4 Fc backbone that lacks effector function. We compared the binding of TTI-602 and TTI-616 to human CD47 using a direct binding assay (FIG. 1A) and an indirect competition assay (FIG. 1B). For the direct binding assay, CD47+ human Jurkat cells were incubated with the various concentrations (as indicated) of hSIRPαFc proteins on ice for 1 hour. The cells were then washed to remove any unbound protein and then incubated with an anti-hIgG Fcg specific (Fab')$_2$ FITC antibody on ice for 1 hour. The cells were then washed and fixed by incubating with a 2% paraformaldehyde solution overnight. The fixing solution was then washed off and the cells were analyzed by flow cytometry (BD FACScan). Data was fit to a one site binding model using nonlinear regression. For the indirect assay, a fixed, saturating amount of biotinylated human SIRPαFc (TTI-601) was incubated either alone or with titrated amounts of TTI-602 or TTI-616 for 15 min on ice. This mixture was then added to human CD47+ Jurkat cells, incubated on ice for 1 hour, washed to remove unbound protein, and then incubated with a saturating amount of streptavidin-PE on ice in the dark for 1 hr. The cells were then washed, fixed and analyzed by flow cytometry as above. The geometric means were then normalized, with 100% inhibition being the geometric mean of the Streptavidin-PE alone and 0% inhibition being the geometric mean of the Biotinylated TTI601 alone. A line of best fit was obtained by nonlinear regression analysis using the sigmoidal dose-response curve fit (Prism, Graphpad).

The data in FIGS. 1A and 1B clearly show a binding difference between TTI-602 and TTI-616, with TTI-616 binding with higher affinity in both assays. In the direct binding assay, TTI-616 bound with 10-fold higher affinity than TTI-602 (EC50 values: 13.4 nM versus 139 nM). In the indirect binding assay, TTI-616 bound with 7-fold higher affinity than TTI-602 (EC$_{50}$ values: 4.5 nM versus 32.1 nM). These results were unexpected, as previously published data indicate that the N-terminal domain of SIRPα bound to CD47 with comparable affinity to SIRPα containing all three extracellular domains (Hatherley et al. 2007 J. Biol. Chem. 282:14567).

2. Design of Human SIRPαFc Fusions with Different Fc Regions

Having established a preference for a fusion protein incorporating a single SIRPα domain, studies were conducted to determine the optimal Fc region. Three different human SIRPαFc fusions were generated that contain the same SIRPα region (31-148) but were constructed on different Fc components which have varying effector activity. The design details are summarized in Table 2 below. The annotated DNA and protein sequences are shown in Appendix 1.

TABLE 2

Design of human SIRPαFc fusion proteins.

| Protein | SIRPα Region | Fc Isotype | Effector Activity |
|---|---|---|---|
| TTI-621 | V2 IgV domain | Human IgG1 (lower hinge-CH2—CH3 domains) | High |
| TTI-622 | V2 IgV domain | Human IgG4 (hinge-CH2—CH3 domains) with Ser-Pro mutation at position 158* | Low |
| TTI-616 | V2 IgV domain | Human IgG4 (hinge-CH2—CH3 domains) with mutations: Ser158Pro*; Glu163Pro; Phe164 Val; Leu165Ala; and deletion of Gly166** | None |

*Corresponds to position 228 in EU numbering system, and is intended to stabilize the IgG4 hinge region and prevent formation of intrachain disulfides leading to monomer formation (Angal et al. 1993 Mol. Immunol. 30: 105)
**Corresponds to positions 233-236 in EU numbering system, and is intended to further reduce Fcγ receptor binding (Armour et al. 1999 Eur. J. Immunol. 29: 2613).

3. Binding of SIRPαFc Fusions to CD47

The three SIRPαFc fusions were compared for binding to cell surface human CD47. Briefly, CD47+ human Jurkat cells were incubated with the various concentrations (as indicated) of hSIRPαFc proteins on ice for 1 hour. The cells were then washed to remove any unbound protein and then incubated with an anti-hIgG Fcg specific (Fab')$_2$ FITC antibody on ice for 1 hour. The cells were then washed and fixed by incubating with a 2% paraformaldehyde solution overnight. The fixing solution was then washed off and the cells were analyzed by flow cytometry (BD FACScan). The geometric means were then normalized and the binding curves and Kd values were generated by Prism (Graphpad) using nonlinear regression fitting the data to a one site binding model.

As shown in FIG. 2, the three fusion proteins showed very similar binding profiles, producing nearly identical affinity binding (Kd) values (2.3-2.4 nM). This was expected, as all three proteins contain the same SIRPα region and the Fc region was not predicted to affect ligand binding.

4. In Vitro Pro-Phagocytosis Activity of SIRPαFc Fusions

Blockade of CD47 by SIRPαFc enhances the phagocytosis of human acute myeloid leukemia (AML) tumor cells by activated human macrophages. The pro-phagocytic activity of the three fusion proteins was compared in vitro to determine if the Fc region affects AML phagocytosis. Human macrophages were generated by first isolating CD14+ monocytes from Ficoll-purified human peripheral blood mononuclear cells using magnetic selection. Monocytes were cultured in X-vivo media containing human monocyte colony stimulating factor at 20 ng/ml for at least 1 week to promote development into macrophages. The macrophages were then plated onto glass slides in a 24-well culture plate and incubated with human interferon gamma overnight. The next day, the wells were washed and LPS was added for at least 1 hour. Human AML cells were counted and labelled with CFSE. After labelling, the AML cells were incubated for 15 min at room temperature (RT) with PBS, SIRPαFc proteins or isotype controls. The AML cells were then added to the individual wells, mixed and incubated in a 37° C., 5% $CO_2$ humidified cell incubator for 2 hours. After the incubation, the wells were washed and the macrophages were labelled with the wheat germ agglutinin Alexa Fluor® 555 conjugate (Invitrogen, cat #W32464) for 15 min at RT with rocking. The wells were then washed and fixed with 2% paraformaldehyde for 30 min at RT. The wells were then washed and kept in dark at 4° C. overnight. The glass slides were analyzed by scanning confocal microscopy (Quorum Wave FX-X1 Spinning Disc Confocal System, Quorum Technologies, Guelph, ON, Canada). The phagocytosis of AML cells was quantified using a phagocytosis index, as follows: (number of AML cells inside macrophages)×100/number of macrophages; counting at least 200 macrophages per sample. As shown in FIG. 3, TTI-621 and TTI-622 exhibit similar pro-phagocytosis activity, whereas TTI-616 is clearly weaker (this is particularly evident at the 10 nM dose). This indicates either a wild type IgG4 or IgG1 Fc region is required for maximal SIRPαFc-triggered tumor cell killing by macrophages.

An expanded panel of SIRPαFc fusion proteins was evaluated for phagocytosis activity using the AML cell line OCI/AML-2 as targets. As shown in FIG. 6, the data clearly indicate that the highest level of AML-2 phagocytosis is induced by fusion proteins containing a single SIRPα domain and a wild type IgG4 or IgG1 Fc region (i.e., TTI-622, -620 or TTI-621). Fusion proteins lacking any Fc effector function (e.g., TTI-616) can trigger phagocytosis, but the effect is considerably weaker. This is consistent with the data reported in FIG. 3. SIRPαFc with three extracellular domains (TTI-601, TTI-602 and R&D) also exhibit only a low level of pro-phagocytic activity, and in the case of the R&D fusion this poor activity cannot be overcome with an IgG1 Fc region. In addition, fusion proteins containing mutated SIRPα sequences that confer substantially higher CD47 binding (TTI-623 and TTI-624) do not result in higher phagocytosis activity compared to a wild type SIRPαFc bearing the same Fc region (TTI-616). These results suggest that increasing the CD47 binding affinity beyond the level achieved with a wild type single SIRPα domain does not result in any further benefit in vitro. This conclusion is unexpected, as it was reported that FD6 and CV1 mutated SIRPα linked to IgG4 Fc have greater pro-phagocytic activity than wild type SIRPα-IgG4 (Weiskopf et al. 2013 Science 341:88).

5. In Vivo Anti-Leukemic Activity of SIRPαFc Fusions

The three SIRPαFc fusion proteins were tested for their ability to control the growth of human AML tumor cells in a standard xenotransplantation model. NOD/ShiLtJ-Prkdc-scid (NOD.SCID) mice (8-12 weeks old) were sublethally irradiated with 275 cGy from a 137Cs γ-irradiator 24 hours before intrafemoral injection of AML cells collected from a human leukemia patient. Starting three weeks after transplantation, mice were treated with SIRPαFc fusion proteins (8 mg/kg IP three times per week) or equimolar doses of control Fc proteins TTI-401 (mutated human IgG4) or TTI-402 (human IgG1). After 4 weeks of treatment, mice were sacrificed and human leukemia cells in the injected femur, non-injected bone marrow and spleen detected by flow cytometric analysis, staining for expression of human CD45 and human CD33 markers. The AML engraftment was expressed as the percentage of human CD45+CD33+ cells in each compartment.

As shown in FIG. 4, the TTI-621 fusion protein bearing an IgG1 Fc region was the only protein capable of mediating an anti-leukemic effect at the site of transplantation (the injected femur). In the non-injected bone marrow, there was a clear Fc dependent effect, with TTI-621 (full Fe activity) >TTI-622 (low Fc activity)>TTI-616 (no Fe activity). All three fusion proteins exhibited anti-leukemic activity in the spleen, although this site is a less rigorous test of activity, as the overall engraftment level (as seen in control mice) is much lower than in the injected or non-injected bone marrow. Collectively, these results indicate that a SIRPαFc protein bearing a human IgG1 Fc region has the greatest activity in a human AML xenotransplantation model. The superior in vivo activity of the IgG1-based fusion would not have been predicted based on the in vitro phagocytosis data (FIG. 2), in which TTI-621 and TTI-622 showed similar activity.

6. Hemagglutination Activity of SIRPαFc Fusions

Human red blood cells were prepared using heparinized whole blood from healthy donors. 4 mL whole blood was pipetted in a 15 mL conical tube, topped up with phosphate buffered saline (PBS) and centrifuged at 200×g, room temperature for 10 minutes to remove the platelets. After aspiration of the platelet fraction the tube was topped up to 15 mL with PBS, the content mixed well by inverting the tube and the RBCs were packed by centrifugation at 1500 rpm for 5 minutes. This wash was repeated 3 more times. After the final wash the supernatant was aspirated and enough PBS was added to the packed erythrocytes to make a 10% RBC solution (for example, if 1 mL packed RBCs were obtained they were further diluted with 9 mL PBS to make a 10% RBC solution). 10% RBC solution stored at 4 C was usable within a week. A fresh 1% RBC solution was made immediately prior to the hemagglutination assay.

SIRPαFc proteins expressed in either CHO or 293 cells were analyzed for their ability to agglutinate human RBCs as evidenced by RBC aggregation and prevention of RBC pellet formation. The assay was performed in 96-well non-tissue culture treated, low protein binding round bottom plates. A fresh 1% RBC solution was made immediately prior to the hemagglutination assay. 50 µL of 1% RBC solution was transferred to each well. 3-fold serially diluted human SIRPa-Fc fusion proteins starting at 3 µM final concentration or vehicle control were added at 50 µL per well to the appropriate wells. Wells were mixed gently and incubated overnight at 37° C., 5% $CO_2$. After an overnight incubation the plates were photographed. In the absence of crosslinking, the erythrocytes roll to the bottom of the wells and appear as a tight pellet. Evidence of hemagglutination is demonstrated by the presence of non-settled RBCs appearing as a haze compared to a well-defined RBC pellet. SIRPa fusion proteins that trigger hemagglutination will prevent the formation of an RBC pellet and thus produce a diffuse or hazy pattern. Results indicate that the three-domain SIRPαFc fusion proteins TTI-601 and TTI-602 show an increased propensity to induce hemagglutination compared to single-domain fusions. This suggests that single-domain SIRPαFcs would be less likely to cause RBC toxicity in vivo.

7. CD47 Agonist Activity of SIRPαFc Fusions

Human Jurkat T cells Clone E6-1 were purchased from ATCC (Cat #TIB-152) and grown in RPMI 1640 supplemented with 10% FBS, 2 mM L-glutamine, 1 mM sodium pyruvate, 10 mM HEPES, and 1.5 g/L sodium bicarbonate. CD47 expression was analysed by flow cytometry by demonstrating cell surface binding of anti-CD47 mAbs clones B6H12, 2D3, BRIC126, and CC2C6. The day prior to an agonist assay Jurkat cells were seeded at ~3×10$^5$ cells/mL in a complete growth media in T75/T150 tissue culture flask.

Highly viable (>95%) Jurkat T cells were harvested and plated out in a complete growth media at 2×10$^5$ cells/200 μL per well in a round bottom 96-well tissue culture plate. Cells were pre-treated with either medium alone or a CD47-blocking antibody clone B6H12 at 12.5 μg/20 μL per well for 1 hour at 37° C., 5% CO$_2$. SIRPaFc fusion proteins or control Fcs were added at 3 μM final concentration in 20 μL/well and the pro-apoptotic agent staurosporine was used as a positive control was added at 1 μM in 20 μL/well. Untreated cells (UT) received 20 μL/well media alone. Cells were incubated overnight at 37° C., 5% CO$_2$. After an overnight incubation the cells were stained with Annexin-V:FITC/7-AAD apoptosis detection kit from eBiosciences (Cat #88-8005-75) following manufacturer's instructions and analyzed by flow cytometry within 4 hours of staining to prevent the progression of apoptosis.

As shown in FIG. 5, TTI-602, a three-domain fusion, induced a much greater level of Jurkat apoptosis than the single-domain fusion proteins TTI-616 and TTI-620. The effect of TTI-602 was clearly CD47-specific, as it was neutralized by pre-treating the cells with B6H12, a CD47-blocking antibody. These results indicate that a single domain SIRPαFc fusion protein is preferred over a three-domain SIRPαFc to minimize CD47 agonist activity.

8. Erythrocyte Binding

One concern with CD47-based therapies is the expression of the target on the surface of red blood cells (RBCs), which has the potential to act as a large antigen sink and cause hematological toxicity. Indeed, anemia has been reported in animals treated with high affinity SIRPαFcs variants and CD47-specific antibodies. The binding of SIRPαFc fusion proteins to human erythrocytes was therefore assessed by flow cytometry. Human RBCs were prepared using heparinized whole blood. Whole blood was centrifuged at 200×g, room temperature for 10 minutes to remove the platelets. After aspiration of the platelet fraction the tube was topped up to the original volume with PBS, the content mixed well by inverting the tube and the RBCs were pelleted by centrifugation at 1500 rpm for 5 minutes. This wash was repeated 3-5 more times. After the final wash the supernatant was aspirated and the tube was topped up with PBS up to the original blood volume. RBCs were counted using haemocytometer and resuspended at 5×10$^8$ cells/mL prior to RBC binding assay. The purity the erythrocytes was assessed by flow cytometry demonstrating anti-human CD235a (eBiosciences Cat #12-9978).

It was observed that fusion proteins containing wild type SIRPα sequences bind very poorly to human erythrocytes, producing a signal that is less than 2-fold above background even at high concentrations. In contrast, CD47 monoclonal antibodies typically bind at >100-fold above background. The striking difference in RBC binding between SIRPαFc and CD47 antibodies is shown in FIG. 7A, which compares the binding of TTI-616 to the CD47 antibody B6H12 over a range of concentrations. To demonstrate that this phenomenon is not unique to B6H12, three additional CD47 antibodies (2D3, BRIC126 and CC2C6) were evaluated. As shown in FIG. 7B, all four antibodies bound human RBCs at dramatically higher levels than SIRPαFc. Note that SIRPαFc fusion proteins bind poorly to human RBCs regardless of Fc isotype or one- or three-domain structure (data not shown). Furthermore, the difference in erythrocyte binding between SIRPαFc and CD47 antibodies does not simply reflect a difference in CD47 affinity, as both classes of proteins bind similarly to an AML tumor cell line (See FIG. 7C).

Several unexpected results were obtained from these studies. First, the superior binding affinity of single domain SIRPαFc compared to a three-domain SIRPαFc is not consistent with the published literature. Second, the strong role for the Fc region in the elimination of leukemic cells in vivo is inconsistent with data published by others, who have argued that the efficacy of CD47 antibodies is due to blockade of the CD47-SIRPα interaction. As well, the superior in vivo efficacy of TTI-621 (IgG1) would not be predicted based on the in vitro phagocytosis data. Moreover, the very low binding of single domain SIRPαFc to erythrocytes, and the low CD47 agonist activity, all support the medical use of the SIRPαFc taught herein in preference to other CD47 inhibitors.

Collectively, these data indicate that an optimal human SIRPαFc fusion protein should contain a single (N-terminal) SIRPα domain linked to an effector competent Fc region, such as the Fc region of a human IgG1 preferably, or the Fc region of a human IgG4 suitably.

We claim:

1. A human SIRPa fusion protein that inhibits the growth and/or proliferation of a CD47[+] disease cell, wherein the SIRPα fusion protein comprises SEQ ID No. 25.

2. A pharmaceutical composition comprising a pharmaceutically acceptable carrier and an amount of a fusion protein according to claim 1 effective to inhibit the growth or proliferation of a CD47[+] disease cell.

3. A human SIRPa fusion protein that inhibits the growth and/or proliferation of a CD47[+] disease cell, wherein the human SIRPa fusion protein consists of SEQ ID No. 25.

4. A pharmaceutical composition comprising a pharmaceutically acceptable carrier and an amount of a fusion protein according to claim 3 effective to inhibit the growth or proliferation of a CD47[+] disease cell.

* * * * *

SEQUENCE LISTING

```
<160> NUMBER OF SEQ ID NOS: 28

<210> SEQ ID NO 1
<211> LENGTH: 106
<212> TYPE: PRT
<213> ORGANISM: Homo sapiens

<400> SEQUENCE: 1

Glu Glu Leu Gln Val Ile Gln Pro Asp Lys Ser Val Ser Val Ala Ala
1               5                   10                  15

Gly Glu Ser Ala Ile Leu His Cys Thr Val Thr Ser Leu Ile Pro Val
            20                  25                  30

Gly Pro Ile Gln Trp Phe Arg Gly Ala Gly Pro Ala Arg Glu Leu Ile
        35                  40                  45

Tyr Asn Gln Lys Glu Gly His Phe Pro Arg Val Thr Thr Val Ser Glu
    50                  55                  60

Ser Thr Lys Arg Glu Asn Met Asp Phe Ser Ile Ser Ile Ser Asn Ile
65                  70                  75                  80
```

```
Thr Pro Ala Asp Ala Gly Thr Tyr Tyr Cys Val Lys Phe Arg Lys Gly
                85                  90                  95

Ser Pro Asp Thr Glu Phe Lys Ser Gly Ala
            100                 105
```

<210> SEQ ID NO 2
<211> LENGTH: 227
<212> TYPE: PRT
<213> ORGANISM: Homo sapiens

<400> SEQUENCE: 2

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225
```

<210> SEQ ID NO 3
<211> LENGTH: 345
<212> TYPE: PRT
<213> ORGANISM: Homo sapiens

<400> SEQUENCE: 3

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
50                  55                  60
```

```
Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser Asp Lys Thr His Thr Cys Pro Pro Cys Pro
        115                 120                 125

Ala Pro Glu Leu Leu Gly Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 4
<211> LENGTH: 375
<212> TYPE: PRT
<213> ORGANISM: Homo sapiens

<400> SEQUENCE: 4

Met Glu Pro Ala Gly Pro Ala Pro Gly Arg Leu Gly Pro Leu Leu Cys
  1               5                  10                  15

Leu Leu Leu Ala Ala Ser Cys Ala Trp Ser Gly Val Ala Gly Glu Glu
                 20                  25                  30

Glu Leu Gln Val Ile Gln Pro Asp Lys Ser Val Ser Val Ala Ala Gly
             35                  40                  45

Glu Ser Ala Ile Leu His Cys Thr Val Thr Ser Leu Ile Pro Val Gly
         50                  55                  60

Pro Ile Gln Trp Phe Arg Gly Ala Gly Pro Ala Arg Glu Leu Ile Tyr
 65                  70                  75                  80

Asn Gln Lys Glu Gly His Phe Pro Arg Val Thr Thr Val Ser Glu Ser
                 85                  90                  95
```

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
            115                 120                 125

Pro Asp Thr Glu Phe Lys Ser Gly Ala Gly Thr Glu Leu Ser Val Arg
130                 135                 140

Ala Lys Pro Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Asp Glu Leu Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
    370                 375

<210> SEQ ID NO 5
<211> LENGTH: 318
<212> TYPE: DNA
<213> ORGANISM: Homo sapiens

<400> SEQUENCE: 5
gaggagctgc aggtgattca gcctgacaag tccgtatcag ttgcagctgg agagtcggcc      60
attctgcact gcactgtgac ctccctgatc cctgtggggc ccatccagtg gttcagagga     120
gctggaccag cccgggaatt aatctacaat caaaaagaag gccacttccc ccgggtaaca     180
actgtttcag agtccacaaa gagagaaaac atggactttt ccatcagcat cagtaacatc     240
accccagcag atgccggcac ctactactgt gtgaagttcc ggaaagggag ccctgacacg     300
gagtttaagt ctggagca                                                   318

<210> SEQ ID NO 6
<211> LENGTH: 684
<212> TYPE: DNA

<213> ORGANISM: Homo sapiens

<400> SEQUENCE: 6

```
gacaaaactc acacatgccc accgtgccca gcacctgaac tcctgggggg accgtcagtc    60
ttcctcttcc caccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcggagg agcagtacaa cagcacgtac    240
cgtgtggtca gcgtcctcac cgtcctgcac caggactggc tgaatggcaa ggagtacaag   300
tgcaaggtct ccaacaaagc cctcccagcc cccatcgaga aaaccatctc caaagccaaa   360
gggcagcccc gagaaccaca ggtgtacacc ctgcccccat cccgggatga gctgaccaag   420
aaccaggtca gcctgacctg cctggtcaaa ggcttctatc ccagcgacat cgccgtggag   480
tgggagagca atgggcagcc ggagaacaac tacaagacca cgcctcccgt gctggactcc   540
gacggctcct tcttcctcta tagcaagctc accgtggaca agagcaggtg gcagcagggg   600
aacgtcttct catgctccgt gatgcatgag gctctgcaca accactacac gcagaagagc   660
ctctccctgt ctccgggtaa atga                                          684
```

<210> SEQ ID NO 7
<211> LENGTH: 1035
<212> TYPE: DNA
<213> ORGANISM: Homo sapiens

<400> SEQUENCE: 7

```
gaggagctgc aggtgattca gcctgacaag tccgtatcag ttgcagctgg agagtcggcc    60
attctgcact gcactgtgac ctccctgatc cctgtggggc ccatccagtg gttcagagga   120
gctggaccag cccgggaatt aatctacaat caaaagaag gccacttccc ccgggtaaca    180
actgtttcag agtccacaaa gagagaaaac atggactttt ccatcagcat cagtaacatc   240
accccagcag atgccggcac ctactactgt gtgaagttcc ggaaagggag ccctgacacg   300
gagtttaagt ctggagcagg cactgagctg tctgtgcgtg ccaaacccct tgacaaaact   360
cacacatgcc caccgtgccc agcacctgaa ctcctggggg gaccgtcagt cttcctcttc   420
ccaccaaaac ccaaggacac cctcatgatc tcccggaccc ctgaggtcac atgcgtggtg   480
gtggacgtga gccacgaaga ccctgaggtc aagttcaact ggtacgtgga cggcgtggag   540
gtgcataatg ccaagacaaa gccgcgggag gagcagtaca acagcacgta ccgtgtggtc   600
agcgtcctca ccgtcctgca ccaggactgg ctgaatggca aggagtacaa gtgcaaggtc   660
tccaacaaag cctcccagc ccatcgag aaaaccatct ccaaagccaa agggcagccc     720
cgagaaccac aggtgtacac cctgcccca tcccggatg agctgaccaa gaaccaggtc    780
agcctgacct gcctggtcaa aggcttctat cccagcgaca tcgccgtgga gtgggagagc   840
aatgggcagc cggagaacaa ctacaagacc acgcctcccg tgctggactc cgacggctcc   900
ttcttcctct atagcaagct caccgtggac aagagcaggt ggcagcaggg gaacgtcttc   960
tcatgctccg tgatgcatga ggctctgcac aaccactaca cgcagaagag cctctccctg  1020
tctccgggta aatga                                                   1035
```

<210> SEQ ID NO 8
<211> LENGTH: 1128
<212> TYPE: DNA
<213> ORGANISM: Homo sapiens

<400> SEQUENCE: 8

-continued

```
atggagcccg ccggcccggc ccccggccgc ctcgggccgc tgctctgcct gctgctcgcc    60
gcgtcctgcg cctggtcagg agtggcgggt gaggaggagc tgcaggtgat tcagcctgac   120
aagtccgtat cagttgcagc tggagagtcg gccattctgc actgcactgt gacctccctg   180
atccctgtgg ggcccatcca gtggttcaga ggagctggac cagcccggga attaatctac   240
aatcaaaaag aaggccactt cccccgggta acaactgttt cagagtccac aaagagagaa   300
aacatggact tttccatcag catcagtaac atcaccccag cagatgccgg cacctactac   360
tgtgtgaagt tccggaaagg gagccctgac acggagttta agtctggagc aggcactgag   420
ctgtctgtgc gtgccaaacc ctctgacaaa actcacacat gcccaccgtg cccagcacct   480
gaactcctgg ggggaccgtc agtcttcctc ttcccaccaa acccaaggga caccctcatg   540
atctcccgga ccccctgaggt cacatgcgtg gtggtggacg tgagccacga agaccctgag   600
gtcaagttca actggtacgt ggacggcgtg gaggtgcata atgccaagac aaagccgcgg   660
gaggagcagt acaacagcac gtaccgtgtg gtcagcgtcc tcaccgtcct gcaccaggac   720
tggctgaatg gcaaggagta caagtgcaag gtctccaaca aagccctccc agcccccatc   780
gagaaaacca tctccaaagc caagggcag ccccgagaac cacaggtgta caccctgccc   840
ccatcccggg atgagctgac caagaaccag gtcagcctga cctgcctggt caaaggcttc   900
tatcccagcg acatcgccgt ggagtgggag agcaatgggc agccggagaa caactacaag   960
accacgcctc ccgtgctgga ctccgacggc tccttcttcc tctatagcaa gctcaccgtg  1020
gacaagagca ggtggcagca ggggaacgtc ttctcatgct ccgtgatgca tgaggctctg  1080
cacaaccact acacgcagaa gagcctctcc ctgtctccgg gtaaatga              1128
```

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ggcgctagcc accatggagc                                                 20

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
ggtgaagctc actgtgtgct g                                               21

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
cagcacacag tgagcttcac c                                               21

<210> SEQ ID NO 12
<211> LENGTH: 20
<212> TYPE: DNA

<213> ORGANISM: Artificial Sequence
<220> FEATURE:
<223> OTHER INFORMATION: primer

<400> SEQUENCE: 12
ccggatcctc atttacccag                                                    20

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
ggactcagag ggtttggcac gcacaga                                            27

<210> SEQ ID NO 14
<211> LENGTH: 27
<212> TYPE: DNA
<213> ORGANISM: Artificial Sequence
<220> FEATURE:
<223> OTHER INFORMATION: primer

<400> SEQUENCE: 14
ccctctgagt ccaaatatgg tccccca                                            27

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
agttttgtca gagggtttgg cacgcacaga                                         30

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
aaaccctctg acaaaactca cacatgccca                                         30

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
cacggatcct catttacccg g                                                  21

<210> SEQ ID NO 18
<211> LENGTH: 27
<212> TYPE: DNA
<213> ORGANISM: Artificial Sequence
<220> FEATURE:
<223> OTHER INFORMATION: primer

<400> SEQUENCE: 18
aggtgctggg catggtgggc atggggg                                            27

<210> SEQ ID NO 19
<211> LENGTH: 27
<212> TYPE: DNA
<213> ORGANISM: Artificial Sequence
<220> FEATURE:
<223> OTHER INFORMATION: primer

<400> SEQUENCE: 19
cccccatgcc caccatgccc agcacct                                27

<210> SEQ ID NO 20
<211> LENGTH: 29
<212> TYPE: DNA
<213> ORGANISM: Artificial Sequence
<220> FEATURE:
<223> OTHER INFORMATION: primer

<400> SEQUENCE: 20
cacggatcct catttaccca gagacaggg                              29

<210> SEQ ID NO 21
<211> LENGTH: 11
<212> TYPE: PRT
<213> ORGANISM: Artificial Sequence
<220> FEATURE:
<223> OTHER INFORMATION: amino acid linker

<400> SEQUENCE: 21

Gly Thr Glu Leu Ser Val Arg Ala Lys Pro Ser
1               5                   10

<210> SEQ ID NO 22
<211> LENGTH: 118
<212> TYPE: PRT
<213> ORGANISM: Homo sapiens

<400> SEQUENCE: 22

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 23
<211> LENGTH: 229
<212> TYPE: PRT
<213> ORGANISM: Homo sapiens

<400> SEQUENCE: 23

Glu Ser Lys Tyr Gly Pro Pro Cys Pro Ser Cys Pro Ala Pro Glu Phe

```
       1               5                  10                 15
Leu Gly Gly Pro Ser Val Phe Leu Phe Pro Lys Pro Lys Asp Thr
                20                  25                 30
Leu Met Ile Ser Arg Thr Pro Glu Val Thr Cys Val Val Asp Val
                35                  40                 45
Ser Gln Glu Asp Pro Glu Val Gln Phe Asn Trp Tyr Val Asp Gly Val
        50                  55                 60
Glu Val His Asn Ala Lys Thr Lys Pro Arg Glu Glu Gln Phe Asn Ser
65                  70                  75                 80
Thr Tyr Arg Val Val Ser Val Leu Thr Val Leu His Gln Asp Trp Leu
                85                  90                 95
Asn Gly Lys Glu Tyr Lys Cys Lys Val Ser Asn Lys Gly Leu Pro Ser
                100                 105                110
Ser Ile Glu Lys Thr Ile Ser Lys Ala Lys Gly Gln Pro Arg Glu Pro
                115                 120                125
Gln Val Tyr Thr Leu Pro Pro Ser Gln Glu Glu Met Thr Lys Asn Gln
        130                 135                140
Val Ser Leu Thr Cys Leu Val Lys Gly Phe Tyr Pro Ser Asp Ile Ala
145                 150                 155                160
Val Glu Trp Glu Ser Asn Gly Gln Pro Glu Asn Asn Tyr Lys Thr Thr
                165                 170                175
Pro Pro Val Leu Asp Ser Asp Gly Ser Phe Phe Leu Tyr Ser Arg Leu
                180                 185                190
Thr Val Asp Lys Ser Arg Trp Gln Glu Gly Asn Val Phe Ser Cys Ser
                195                 200                205
Val Met His Glu Ala Leu His Asn His Tyr Thr Gln Lys Ser Leu Ser
        210                 215                220
Leu Ser Leu Gly Lys
225

<210> SEQ ID NO 24
<211> LENGTH: 229
<212> TYPE: PRT
<213> ORGANISM: Homo sapiens

<400> SEQUENCE: 24

Glu Ser Lys Tyr Gly Pro Pro Cys Pro Pro Cys Pro Ala Pro Glu Phe
1               5                   10                 15
Leu Gly Gly Pro Ser Val Phe Leu Phe Pro Lys Pro Lys Asp Thr
                20                  25                 30
Leu Met Ile Ser Arg Thr Pro Glu Val Thr Cys Val Val Asp Val
                35                  40                 45
Ser Gln Glu Asp Pro Glu Val Gln Phe Asn Trp Tyr Val Asp Gly Val
        50                  55                 60
Glu Val His Asn Ala Lys Thr Lys Pro Arg Glu Glu Gln Phe Asn Ser
65                  70                  75                 80
Thr Tyr Arg Val Val Ser Val Leu Thr Val Leu His Gln Asp Trp Leu
                85                  90                 95
Asn Gly Lys Glu Tyr Lys Cys Lys Val Ser Asn Lys Gly Leu Pro Ser
                100                 105                110
Ser Ile Glu Lys Thr Ile Ser Lys Ala Lys Gly Gln Pro Arg Glu Pro
                115                 120                125
Gln Val Tyr Thr Leu Pro Pro Ser Gln Glu Glu Met Thr Lys Asn Gln
        130                 135                140
```

```
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 25
<211> LENGTH: 345
<212> TYPE: PRT
<213> ORGANISM: Homo sapiens

<400> SEQUENCE: 25

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285
```

```
Tyr Lys Thr Thr Pro Val Leu Asp Ser Asp Gly Ser Phe Phe Leu
        290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 26
<211> LENGTH: 347
<212> TYPE: PRT
<213> ORGANISM: Homo sapiens

<400> SEQUENCE: 26

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Glu Ser Lys Tyr Gly Pro Pro Cys Pro Pro
        115                 120                 125

Cys Pro Ala Pro Glu Phe Leu Gly Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Arg Leu Thr Val Asp Lys Ser Arg Trp Gln Glu Gly
```

| | | | | |
|---|---|---|---|---|
|305| |310| |315| |320|

Asn Val Phe Ser Cys Ser Val Met His Glu Ala Leu His Asn His Tyr
                325                 330                 335

Thr Gln Lys Ser Leu Ser Leu Ser Leu Gly Lys
        340                 345

```
<210> SEQ ID NO 27
<211> LENGTH: 1128
<212> TYPE: DNA
<213> ORGANISM: Homo sapiens

<400> SEQUENCE: 27
atggagcccg ccggcccggc ccccggccgc ctcgggccgc tgctctgcct gctgctcgcc      60
gcgtcctgcg cctggtcagg agtggcgggt gaggaggagc tgcaggtgat tcagcctgac     120
aagtccgtat cagttgcagc tggagagtcg gccattctgc actgcactgt gacctccctg     180
atccctgtgg ggcccatcca gtggttcaga ggagctggac cagcccggga attaatctac     240
aatcaaaaag aaggccactt cccccgggta acaactgttt cagagtccac aaagagagaa     300
aacatggact tttccatcag catcagtaac atcaccccag cagatgccgg cacctactac     360
tgtgtgaagt tccggaaagg gagccctgac acggagttta gtctggagc aggcactgag      420 ctgtctgtgc gtgccaaacc ctctgacaaa actcacacat gcccaccgtg cccagcacct     480
gaactcctgg ggggaccgtc agtcttcctc ttccccccaa aacccaagga caccctcatg     540
atctcccgga cccctgaggt cacatgcgtg gtggtggacg tgagccacga agaccctgag     600
gtcaagttca actggtacgt ggacggcgtg gaggtgcata atgccaagac aaagccgcgg     660
gaggagcagt acaacagcac gtaccgtgtg gtcagcgtcc tcaccgtcct gcaccaggac     720
tggctgaatg gcaaggagta caagtgcaag gtctccaaca aagccctccc agcccccatc     780
gagaaaacca tctccaaagc caaagggcag ccccgagaac acaggtgta cacccttgccc     840 ccatcccggg atgagctgac caagaaccag gtcagcctga cctgcctggt caaaggcttc     900
tatcccagcg acatcgccgt ggagtgggag agcaatgggc agccggagaa caactacaag     960
accacgcctc ccgtgctgga ctccgacggc tccttcttcc tctatagcaa gctcaccgtg    1020
gacaagagca ggtggcagca ggggaacgtc ttctcatgct ccgtgatgca tgaggctctg    1080
cacaaccact acacgcagaa gagcctctcc ctgtctccgg gtaaatga                 1128

<210> SEQ ID NO 28
<211> LENGTH: 1134
<212> TYPE: DNA
<213> ORGANISM: Homo sapiens

<400> SEQUENCE: 28
atggagcccg ccggcccggc ccccggccgc ctcgggccgc tgctctgcct gctgctcgcc      60
gcgtcctgcg cctggtcagg agtggcgggt gaggaggagc tgcaggtgat tcagcctgac     120
aagtccgtat cagttgcagc tggagagtcg gccattctgc actgcactgt gacctccctg     180
atccctgtgg ggcccatcca gtggttcaga ggagctggac cagcccggga attaatctac     240
aatcaaaaag aaggccactt cccccgggta acaactgttt cagagtccac aaagagagaa     300
aacatggact tttccatcag catcagtaac atcaccccag cagatgccgg cacctactac     360
tgtgtgaagt tccggaaagg gagccctgac acggagttta gtctggagc aggcactgag      420 ctgtctgtgc gtgccaaacc ctctgagtcc aaatatggtc cccatgccc accatgccca      480 gcacctgagt tcctggggg accatcagtc ttcctgttcc ccccaaaacc caaggacact      540
```

-continued

```
ctcatgatct cccggacccc tgaggtcacg tgcgtggtgg tggacgtgag ccaggaagac     600
cccgaggtcc agttcaactg gtacgtggat ggcgtggagg tgcataatgc caagacaaag    660
ccgcgggagg agcagttcaa cagcacgtac cgtgtggtca gcgtcctcac cgtcctgcac    720
caggactggc tgaacggcaa ggagtacaag tgcaaggtct ccaacaaagg cctcccgtcc    780
tccatcgaga aaaccatctc caaagccaaa gggcagcccc gagagccaca ggtgtacacc    840
ctgcccccat cccaggagga gatgaccaag aaccaggtca gcctgacctg cctggtcaag    900
ggcttctacc ccagcgacat cgccgtggag tgggagagca atgggcagcc ggagaacaac    960
tacaagacca cgcctcccgt gctggactcc gacggctcct tcttcctcta cagcaggcta   1020
accgtggaca gagcaggtg gcaggagggg aatgtcttct catgctccgt gatgcatgag    1080
gctctgcaca accactacac gcagaagagc ctctccctgt ctctgggtaa atga         1134
```